(12) United States Patent
McCann et al.

(10) Patent No.: US 10,125,042 B2
(45) Date of Patent: Nov. 13, 2018

(54) SYSTEMS FOR MONITORING GLASS AND/OR GLASS FOAM DENSITY AS A FUNCTION OF VERTICAL POSITION WITHIN A VESSEL

(71) Applicant: JOHNS MANVILLE, Denver, CO (US)

(72) Inventors: Jonathan McCann, Orchard Park, NY (US); Jeffrey M Shock, Castle Rock, CO (US); Bryan Keith Nesti, Parker, CO (US); John Euford Mobley, Lexington, TN (US)

(73) Assignee: Johns Manville, Denver, CO (US)

( * ) Notice: Subject to any disclaimer, the term of this patent is extended or adjusted under 35 U.S.C. 154(b) by 22 days.

(21) Appl. No.: 14/801,364

(22) Filed: Jul. 16, 2015

(65) Prior Publication Data

US 2015/0321938 A1    Nov. 12, 2015

Related U.S. Application Data

(62) Division of application No. 13/752,672, filed on Jan. 29, 2013, now Pat. No. 9,115,017.

(51) Int. Cl.
  *C03B 5/24* (2006.01)
  *C03B 5/235* (2006.01)
  *G01N 9/24* (2006.01)

(52) U.S. Cl.
  CPC .............. *C03B 5/24* (2013.01); *C03B 5/2356* (2013.01); *G01N 9/24* (2013.01)

(58) Field of Classification Search
  CPC ......... C03B 5/2356; C03B 5/24; C03B 5/245; C03B 2211/00; C03B 2211/20; C03B 2211/23

(Continued)

(56) References Cited

U.S. PATENT DOCUMENTS 1,706,857 A * 3/1929 Mathe ................. G01F 23/292
                                                  356/623
2,174,533 A   10/1939 See et al.
(Continued)

FOREIGN PATENT DOCUMENTS

DE   36 29 965 A1   3/1988
EP   2 397 446 A2   12/2011
(Continued)

OTHER PUBLICATIONS

English language machine translatoin of DE3629965—espacenet Jun. 24, 2016.*

(Continued)

*Primary Examiner* — Jason L Lazorcik
(74) *Attorney, Agent, or Firm* — Robert D. Touslee

(57) ABSTRACT

Methods and systems for determining density or density gradient of molten foamed glass in a glass melter, an apparatus downstream of a glass melter, or both. A molten foamed glass is generated having molten glass and bubbles entrained therein and/or a layer of glass foam on a top surface thereof in a melter. At least a portion of the molten foamed glass is transferred into an apparatus positioned downstream of the melter, and the density or density gradient of the molten foamed glass in the melter or downstream apparatus is determined as a function of distance from a structural feature of the melter or downstream apparatus, or both, using one or more electromagnetic (EM) wave-based sensors.

24 Claims, 10 Drawing Sheets

(58) Field of Classification Search
USPC .............................................. 65/29.17, 29.18
See application file for complete search history.

(56) References Cited

U.S. PATENT DOCUMENTS

| | | | |
|---|---|---|---|
| 2,269,459 A | 1/1942 | Kleist | |
| 2,432,942 A | 12/1947 | See et al. | |
| 3,170,781 A | 2/1965 | Keefer | |
| 3,237,929 A | 3/1966 | Plumat et al. | |
| 3,245,769 A | 4/1966 | Eck et al. | |
| 3,260,587 A | 7/1966 | Dolf et al. | |
| 3,268,313 A | 8/1966 | Burgman et al. | |
| 3,325,298 A | 6/1967 | Brown | |
| 3,421,873 A | 1/1969 | Burgman et al. | |
| 3,482,956 A * | 12/1969 | Trethewey | C03B 5/24 65/134.5 |
| 3,510,393 A | 5/1970 | Burgman et al. | |
| 3,519,412 A | 7/1970 | Olink | |
| 3,563,683 A | 2/1971 | Hess | |
| 3,573,016 A * | 3/1971 | Rees | C03B 3/00 65/160 |
| 3,573,017 A * | 3/1971 | Griem, Jr. | C03B 3/00 65/162 |
| 3,592,623 A | 7/1971 | Shepherd | |
| 3,606,825 A | 9/1971 | Johnson | |
| 3,617,234 A | 11/1971 | Hawkins et al. | |
| 3,627,504 A | 12/1971 | Johnson et al. | |
| 3,738,792 A | 6/1973 | Feng | |
| 3,741,656 A * | 6/1973 | Shapiro | G01F 23/2928 117/201 |
| 3,741,742 A * | 6/1973 | Jennings | C03B 3/00 65/29.16 |
| 3,746,527 A | 7/1973 | Knavish et al. | |
| 3,764,287 A | 10/1973 | Brocious | |
| 3,771,988 A | 11/1973 | Starr | |
| 3,885,945 A | 5/1975 | Rees et al. | |
| 3,897,232 A * | 7/1975 | Groves | C03B 5/245 65/160 |
| 3,951,635 A | 4/1976 | Rough | |
| 3,976,464 A | 8/1976 | Wardlaw | |
| 4,004,903 A | 1/1977 | Daman et al. | |
| 4,110,098 A | 8/1978 | Mattmuller | |
| 4,185,982 A | 1/1980 | Schwenninger | |
| 4,203,761 A | 5/1980 | Rose | |
| 4,226,564 A | 10/1980 | Takahashi et al. | |
| 4,282,023 A | 8/1981 | Hammel et al. | |
| 4,303,435 A | 12/1981 | Sleighter | |
| 4,309,204 A | 1/1982 | Brooks | |
| 4,323,718 A | 4/1982 | Buhring et al. | |
| 4,349,376 A | 9/1982 | Dunn et al. | |
| 4,397,692 A | 9/1983 | Ramge et al. | |
| 4,406,683 A | 9/1983 | Demarest | |
| 4,432,780 A | 2/1984 | Propster et al. | |
| 4,461,576 A * | 7/1984 | King | G01F 23/292 250/559.24 |
| 4,508,970 A * | 4/1985 | Ackerman | G01F 23/2928 117/15 |
| 4,539,034 A | 9/1985 | Hanneken | |
| 4,542,106 A | 9/1985 | Sproull | |
| 4,718,931 A * | 1/1988 | Boettner | C03B 3/00 65/134.5 |
| 4,723,708 A | 2/1988 | Berger et al. | |
| 4,735,642 A | 4/1988 | Jensen et al. | |
| 4,738,938 A | 4/1988 | Kunkle et al. | |
| 4,758,259 A | 7/1988 | Jensen | |
| 4,816,056 A | 3/1989 | Tsai et al. | |
| 4,886,539 A | 12/1989 | Gerutti et al. | |
| 4,963,731 A * | 10/1990 | King | C03B 5/245 250/559.2 |
| 5,011,086 A | 4/1991 | Sonnleiter | |
| 5,052,874 A | 10/1991 | Johanson | |
| 5,169,424 A | 12/1992 | Grinnen et al. | |
| 5,194,747 A * | 3/1993 | Culpepper | G01F 23/292 250/577 |
| 5,405,082 A | 4/1995 | Brown et al. | |
| 5,473,885 A | 12/1995 | Hunter, Jr. et al. | |
| 5,613,994 A | 3/1997 | Muniz et al. | |
| 5,713,668 A | 2/1998 | Lunghofer et al. | |
| 5,714,121 A | 2/1998 | Alderete et al. | |
| 5,718,741 A | 2/1998 | Hull et al. | |
| 5,849,058 A | 12/1998 | Takeshita et al. | |
| 5,887,978 A | 3/1999 | Lunghofer et al. | |
| 5,944,864 A | 8/1999 | Hull et al. | |
| 6,036,480 A | 3/2000 | Hughes et al. | |
| 6,156,285 A | 12/2000 | Adams et al. | |
| 6,210,703 B1 | 4/2001 | Novich | |
| 6,244,197 B1 | 6/2001 | Coble | |
| 6,274,164 B1 | 8/2001 | Novich | |
| 6,314,760 B1 | 11/2001 | Chenoweth | |
| 6,332,339 B1 | 12/2001 | Kawaguchi et al. | |
| 6,344,747 B1 | 2/2002 | Lunghofer et al. | |
| 6,460,376 B1 | 10/2002 | Jeanvoine et al. | |
| 6,536,238 B2 | 3/2003 | Kawaguchi et al. | |
| 6,578,779 B2 | 6/2003 | Dion | |
| 6,715,319 B2 | 4/2004 | Barrow et al. | |
| 6,739,152 B2 | 5/2004 | Jeanvoine et al. | |
| 6,854,290 B2 | 2/2005 | Hayes et al. | |
| 6,857,999 B2 | 2/2005 | Jeanvoine | |
| 6,883,349 B1 | 4/2005 | Jeanvoine | |
| 7,134,300 B2 | 11/2006 | Hayes et al. | |
| 7,273,583 B2 | 9/2007 | Rue et al. | |
| 7,383,698 B2 | 6/2008 | Ichinose et al. | |
| 7,392,668 B2 | 7/2008 | Adms et al. | |
| 7,428,827 B2 | 9/2008 | Maugendre et al. | |
| 7,448,231 B2 | 11/2008 | Jeanvoine et al. | |
| 7,509,819 B2 | 3/2009 | Baker et al. | |
| 7,565,819 B2 | 7/2009 | Jeanvoine et al. | |
| 7,622,677 B2 | 11/2009 | Barbarree et al. | |
| 8,033,254 B2 | 10/2011 | Hannum et al. | |
| 8,487,262 B2 * | 7/2013 | Damm | G01F 23/288 250/357.1 |
| 8,650,914 B2 | 2/2014 | Charbonneau | |
| 8,707,739 B2 | 4/2014 | Huber et al. | |
| 8,707,740 B2 | 4/2014 | Huber et al. | |
| 8,769,992 B2 | 7/2014 | Huber | |
| 8,875,544 B2 | 11/2014 | Charbonneau | |
| 8,973,400 B2 | 3/2015 | Charbonneau et al. | |
| 8,973,405 B2 | 3/2015 | Charbonneau et al. | |
| 8,991,215 B2 | 3/2015 | Shock et al. | |
| 8,997,525 B2 | 4/2015 | Shock et al. | |
| 9,021,838 B2 | 5/2015 | Charbonneau et al. | |
| 9,032,760 B2 | 5/2015 | Charbonneau et al. | |
| 9,096,452 B2 | 8/2015 | Charbonneau et al. | |
| 9,096,453 B2 | 8/2015 | Charbonneau | |
| 2002/0162358 A1 | 11/2002 | Jeanvoine et al. | |
| 2004/0025569 A1 * | 2/2004 | Damm | G01F 23/288 73/32 R |
| 2004/0128098 A1 * | 7/2004 | Neuhaus | G01F 23/00 702/122 |
| 2004/0168474 A1 | 9/2004 | Jeanvoine et al. | |
| 2004/0224833 A1 | 11/2004 | Jeanvoine et al. | |
| 2005/0061030 A1 * | 3/2005 | Ichinose | C03B 5/193 65/29.17 |
| 2005/0236747 A1 | 10/2005 | Rue et al. | |
| 2006/0000239 A1 | 1/2006 | Jeanvoine et al. | |
| 2006/0138330 A1 * | 6/2006 | Baldwin | G01T 1/167 250/357.1 |
| 2007/0122332 A1 | 5/2007 | Jacques et al. | |
| 2007/0212546 A1 | 9/2007 | Jeanvoine et al. | |
| 2007/0220922 A1 | 9/2007 | Bauer et al. | |
| 2007/0278404 A1 * | 12/2007 | Spanke | G01F 23/0061 250/303 |
| 2008/0256981 A1 | 10/2008 | Jacques et al. | |
| 2008/0276652 A1 | 11/2008 | Bauer et al. | |
| 2009/0042709 A1 | 2/2009 | Jeanvoine et al. | |
| 2011/0048125 A1 * | 3/2011 | Jackson | G01F 23/2885 73/290 R |
| 2011/0088432 A1 | 4/2011 | Purnode et al. | |
| 2011/0308280 A1 | 12/2011 | Huber | |
| 2012/0033792 A1 * | 2/2012 | Kulik | G01N 9/24 378/89 |
| 2012/0077135 A1 | 3/2012 | Charbonneau | |

(56) References Cited

U.S. PATENT DOCUMENTS

| | | | |
|---|---|---|---|
| 2013/0123990 A1* | 5/2013 | Kulik | G01N 9/24 700/275 |
| 2013/0283861 A1 | 10/2013 | Mobley et al. | |
| 2014/0090422 A1 | 4/2014 | Charbonneau et al. | |
| 2014/0090423 A1 | 4/2014 | Charbonneau et al. | |

FOREIGN PATENT DOCUMENTS

| | | |
|---|---|---|
| EP | 2 433 911 A1 | 3/2012 |
| GB | 1449439 | 9/1976 |
| WO | 2010011701 A2 | 1/2010 |

OTHER PUBLICATIONS

"Glass Technologies—The Legacy of a Successful Public-Private Partnership", 2007, U.S. Department of Energy, pp. 1-32.

Rue, "Energy-Efficient Glass Melting—The Next Generation Melter", Gas Technology Institute, Project No. 20621 Final Report (2008).

"Glass Industry of the Future", United States Department of Energy, report 02-GA50113-03, pp. 1-17, Sep. 30, 2008.

Stevenson, "Foam Engineering: Fundamentals and Applications", Chapter 16, pp. 336-389, John Wiley & Sons (Mar. 13, 2012).

Clare et al., "Density and Surface Tension of Borate Containing Silicate Melts", Glass Technology—European Journal of Glass Science and Technology, Part A, pp. 59-62, vol. 44, No. 2, Apr. 1, 2003.

Seward, T.P., "Modeling of Glass Making Processes for Improved Efficiency", DE-FG07-96EE41262, Final Report, dated Mar. 31, 2003.

Conradt et al, Foaming behavior on glass melts, Glastechniche Berichte 60 (1987) Nr. 6, S. 189-201 Abstract Fraunhofer ISC.

Kim et al., "Foaming in Glass Melts Produced by Sodium Sulfate Decomposition under Isothermal Conditions", Journal of the American Ceramic Society, 74(3), pp, 551-555, 1991.

Kim et al., "Foaming in Glass Melts Produced by Sodium Sulfate Decomposition under Ramp Heating Conditions", Journal of the American Ceramic Society, 75(11), pp. 2959-2963, 1992.

Kim et al., "Effect of Furnace Atmosphere on E-glass Foaming", Journal of Non-Crystalline Solids, 352(50/51), pp. 5287-5295, 2006.

Van Limpt et al., "Modelling the evaporation of boron species. Part 1. Alkali-free borosilicate glass melts", Glass Technology—European Journal of Glass Science and Technology, Part A, 52(3): pp, 77-87, 2011.

"Gamma Irradiators for Radiation Processing" Booklet, International Atomic Energy Agency, Vienna, Austria.

Gerber, J., "Les Densimetres Industriels," Petrole et Techniques, Association Francaise des Techniciens du Petrole, Jun. 1, 1989, pp. 26-27, No. 349, Paris, France.

Rue et al, "Submerged Combustion Melting of Glass," International Journal of Applied Glass Science, Nov. 9, 2011, pp. 262-274, vol. 2. No. 4.

Choi et al, Determination of HLW Glass Melt Rate Using X-Ray Computed Tomography (CT), Savannah River National Laboratyr, US DOE contract No. DE-AC09-08SR22470, Oct. 2011.

* cited by examiner

SYSTEMS FOR MONITORING GLASS AND/OR GLASS FOAM DENSITY AS A FUNCTION OF VERTICAL POSITION WITHIN A VESSEL

CROSS-REFERENCE TO RELATED APPLICATIONS

This application is a division of U.S. patent application Ser. No. 13/752,672 filed Jan. 29, 2013, now issued U.S. Pat. No. 9,115,017.

BACKGROUND OF THE INVENTION

The present disclosure relates generally to the field of submerged combustion furnaces and methods of use thereof to produce molten glass, and more specifically to methods and systems for monitoring glass and/or glass foam density as a function of vertical position within a vessel downstream of a submerged combustion melter.

A submerged combustion melter (SCM) may be employed to melt glass batch materials to produce molten glass by passing oxygen, oxygen-enriched mixtures, or air along with a liquid or gaseous fuel, or particulate fuel in the glass batch, directly into a molten pool of glass usually through burners submerged in a glass melt pool. The introduction of high flow rates of products of combustion of the oxidant and fuel into the molten glass, and the expansion of the gases cause rapid melting of the glass batch and much turbulence, and possibly foaming.

Molten glass produced by an SCM is typically about 30 percent void fraction with small bubbles evenly distributed throughout the molten mass of glass. These are referred to herein as "entrained bubbles." This void fraction is much higher than molten glass produced by traditional, non-submerged combustion melters. When molten glass contains a large amount of bubbles, or has a layer of foam floating on top, or both of these conditions exist, it can be extremely difficult to ascertain the local and bulk distribution (size and/or location) of bubbles within the molten glass, and therefore the local and bulk glass density and/or glass foam density, with existing level or depth measuring techniques. When this determination cannot be made accurately, less efficient operation of glass refining equipment and/or the submerged combustion melter may result. For example, if the distribution of bubbles is not known with great confidence, it must be assumed other hand, if the amount and/or distribution of bubbles in the molten glass is underestimated, the resulting glass may be "underlined" and need to be reprocessed, or at worst, discarded as waste.

At least for these reasons, it would be an advance in the glass manufacturing art using melters if density and/or density gradient of the molten glass and/or glass foam produced during melting of glass-forming materials could be monitored in melters and/or equipment downstream of glass melters, in particular submerged combustion melters and equipment downstream thereof. Monitoring density of the molten glass and/or glass foam may also allow new or revised control schemes for the melter itself, and/or the equipment downstream of the melter.

SUMMARY

In accordance with the present disclosure, systems and methods are described for monitoring density and/or density gradient of molten glass and/or glass foam produced during melting of glass-forming materials and/or in equipment downstream of a melter, in particular in submerged combustion melters and/or equipment downstream thereof.

A first aspect of the disclosure is a method comprising:
generating a molten foamed glass comprising molten glass and bubbles entrained therein and/or a layer of glass foam on a top surface thereof in a melter, the melter comprising at least a floor and a sidewall structure defining an internal space sufficient for containing the molten foamed glass;

transferring at least a portion of the molten foamed glass into a downstream apparatus positioned downstream of the melter, the downstream apparatus comprising at least a floor and a sidewall structure defining an internal space sufficient for containing a non-flowing or flowing stream of the molten foamed glass; and determining density as a function of distance from a structural feature (such as a floor or sidewall) of the molten foamed glass in either the melter, the downstream apparatus or both, using one or more electromagnetic (EM) wave-based sensors. In certain embodiments, the method comprises determining a density gradient as a function of distance from the floor of the melter or the downstream apparatus, or both, of the molten foamed glass using one or more electromagnetic (EM) wave-based sensors.

A second aspect of the disclosure is a method comprising:
generating a turbulent molten foamed glass comprising molten glass and bubbles entrained therein and/or a layer of glass foam on a top surface thereof in a submerged combustion melter, the melter comprising at least a floor and a sidewall structure defining an internal space sufficient for containing the turbulent molten foamed glass;

transferring at least a portion of the molten foamed glass into a downstream apparatus positioned downstream of the submerged combustion melter, the downstream apparatus comprising at least a floor and a sidewall structure defining an internal space sufficient for containing a non-flowing or flowing stream of the molten foamed glass; and determining density as a function of distance from a structural feature of the turbulent molten foamed glass in the melter, the downstream apparatus or both, using one or more electromagnetic (EM) wave-based sensors. In certain embodiments, the method comprises determining a density gradient as a function of distance from the floor of the melter or the downstream apparatus, or both, of the turbulent molten foamed glass using one or more electromagnetic (EM) wave-based sensors.

A third aspect of the disclosure is a system comprising:
a melter comprising a floor, a roof, and a wall structure connecting the floor and roof, configured to generate a molten foamed glass (comprising molten glass and bubbles entrained therein and/or a layer of glass foam on a top surface thereof);

a downstream apparatus positioned downstream of and fluidly connected to the melter, the downstream apparatus comprising at least a floor and a sidewall structure defining an internal space sufficient for containing a non-flowing or flowing stream of the molten foamed glass; and one or more EM wave-based sensors a configured and positioned to determine density of the molten foamed glass in either the melter, the downstream apparatus, or both as a function of distance from a structural feature of the melter or downstream apparatus, or both. In certain embodiments, one or more electromagnetic (EM) wave-based sensors are configured and positioned to determine a density gradient as a function of distance from the floor of the melter or the downstream apparatus, or both, of the molten foamed glass.

A fourth aspect of the disclosure is a system comprising: a submerged combustion melter comprising a floor, a roof, and a melter sidewall structure connecting the floor and roof, the melter configured to define an internal space for generating a turbulent molten foamed glass, the submerged combustion melter comprising at least one combustion burner positioned in the floor, the roof, and/or the sidewall structure from which emanates combustion products that intimately contact the molten foamed glass and provide the turbulent molten foamed glass;

a downstream apparatus positioned downstream of and fluidly connected to the submerged combustion melter, the downstream apparatus comprising at least a floor and a sidewall structure defining an internal space sufficient for containing a non-flowing or flowing stream of the molten foamed glass, the foamed glass having a density gradient; and one or more EM wave-based sensors a configured and positioned to determine density of the molten foamed glass in either the melter, the downstream apparatus, or both as a function of distance from a structural feature of the melter or downstream apparatus, or both. In certain embodiments, one or more electromagnetic (EM) wave-based sensors are configured and positioned to determine a density gradient as a function of distance from the floor of the melter or the downstream apparatus, or both, of the molten foamed glass.

Certain systems and methods may be used to measure density in a particular location of the melter using a stationary source and stationary detector, for example near an interface between foam and liquid molten glass. Systems and methods of this disclosure will become more apparent upon review of the brief description of the drawings, the detailed description of the disclosure, and the claims that follow.

BRIEF DESCRIPTION OF THE DRAWINGS

The manner in which the objectives of the disclosure and other desirable characteristics can be obtained is explained in the following description and attached drawings in which:

FIG. 10 is a graph of "percent glass" at a given height in a downstream apparatus vs. time in hours for an embodiment where both EM source and detector are stationary during an operation to determine density gradient of foamed glass, while

Figure 1:
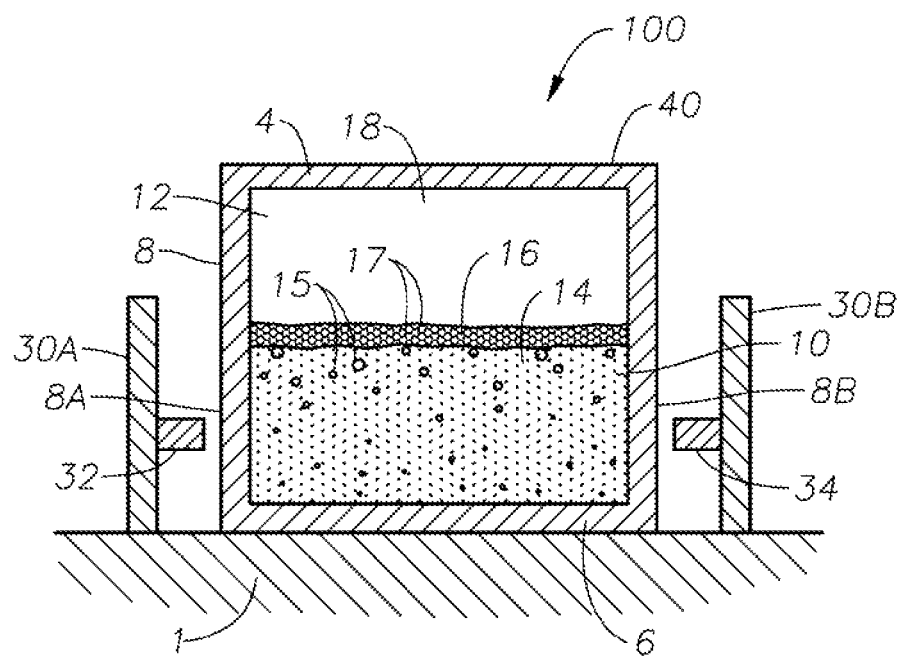
FIGS. 1, 2, 3, 4, 6, 7, and 8 are schematic transverse cross-sectional views of seven non-limiting alternative system embodiments in accordance with the present disclosure, with FIGS. 6A, 6B, 7A, and 7B illustrating further possible variations on the embodiments illustrated in FIGS. 6 and 7.
Figure 2:
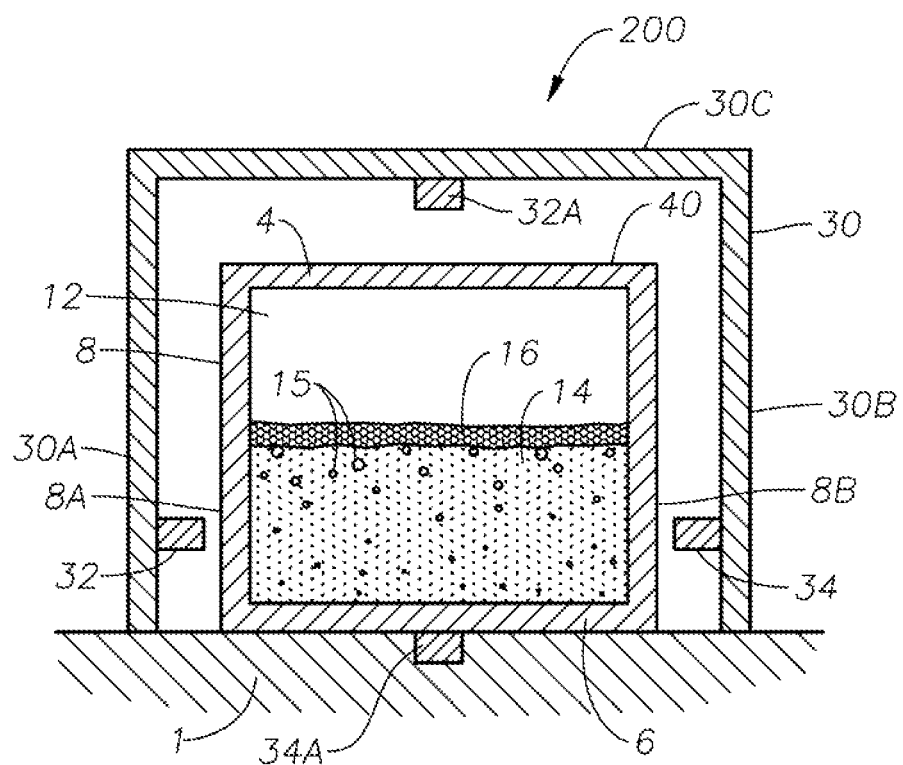
Figure 3:
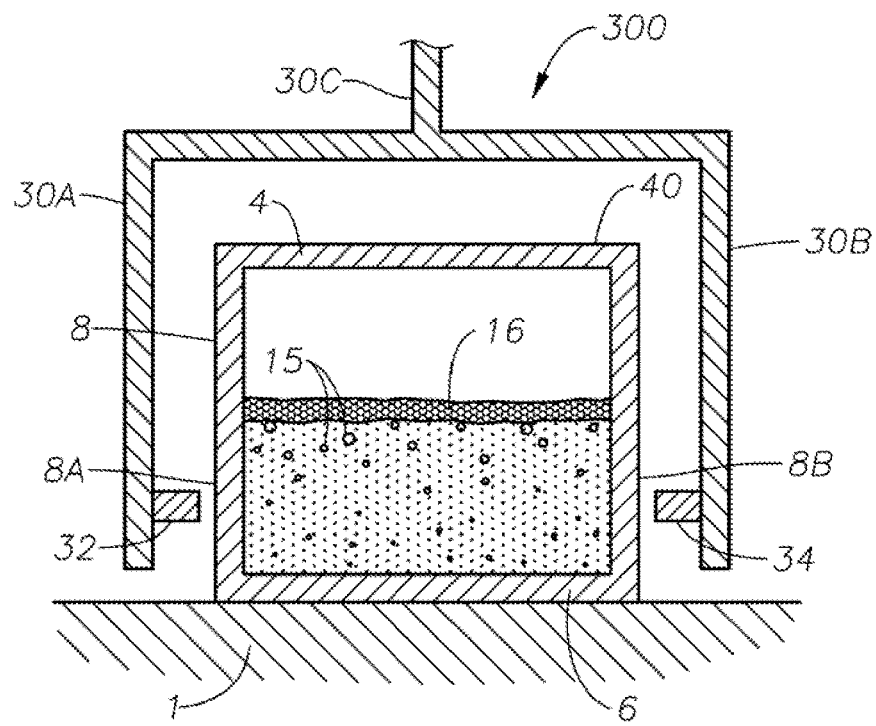

It is to be noted, however, that the appended drawings of FIGS. 1-8 may not be to scale and illustrate only typical embodiments of this disclosure, and are therefore not to be considered limiting of its scope, for the disclosure may admit to other equally effective embodiments.

DETAILED DESCRIPTION

In the following description, numerous details are set forth to provide an understanding of the disclosed systems and methods. However, it will be understood by those skilled in the art that the systems and methods covered by the claims may be practiced without these details and that numerous variations or modifications from the specifically described embodiments may be possible and are deemed within the claims. All U.S. published patent applications and U.S. patents referenced herein are hereby explicitly incorporated herein by reference. In the event definitions of terms in the referenced patents and applications conflict with how those terms are defined in the present application, the definitions for those terms that are provided in the present application shall be deemed controlling.

As explained briefly in the Background, molten glass produced by an SCM is typically about 30 percent void fraction or more with bubbles distributed throughout the molten mass of glass, and this void fraction is much higher than molten glass produced by traditional, non-submerged combustion melters. When molten glass contains a large amount of bubbles, or has a layer of foam floating on top, or both of these conditions exist, it can be extremely difficult to ascertain the local and bulk distribution (size and/or location) of bubbles within the molten glass, and therefore the local density may vary significantly from the bulk glass density and/or glass foam density. When determination of the "density gradient", or how the density varies with depth, cannot be made accurately, less efficient operation of glass refining equipment and/or the submerged combustion melter may result. For example, if the distribution of bubbles is not known with great confidence, it must be assumed that more aggressive fining is required than may actually be necessary to achieve the desire glass composition and density. This "overfining" may be wasteful of energy, fining chemicals, and time. On the other hand, if the amount and/or distribution of bubbles in the molten glass is underestimated, the resulting glass may be "underfined" and need to be reprocessed, or at worst, discarded as waste.

It has been discovered that the density gradient may be determined using one or more methods and systems of the present disclosure. Methods and systems of the present disclosure may provide both quantitative and qualitative information regarding the amount of foam and/or bubbles with the molten glass as a function of distance from the bottom of the particular vessel or downstream apparatus that the molten foamed glass resides in or is flowing through.

Various terms are used throughout this disclosure. Methods and systems of the present disclosure utilize an electromagnetic (EM) sensor having one or more EM sources and one or more EM detectors. When the terms "EM sensor" and "sensor" are used, they will be understood to mean a device having at least one EM source and at least one EM detector. In certain embodiments the EM source may be referred to as a nuclear source. The electromagnetism may be referred to as radiation, and may be in wave, particle and wave/particle formats. In other words, the radiation making up the electromagnetism may have wave properties and/or particle properties. Examples of EM wave radiation include X-ray radiation and gamma ray radiation. The term "EM wave" will be used herein to simplify the discussion, but it will be understood that the radiation could be particle radiation in certain embodiments. The EM source or sources and EM detector or detectors provide feedback on the density gradient of the molten glass in a vessel. This may be accomplished in a variety of ways. In certain embodiments the EM source and EM detector may be simultaneously moved in such a way along an outside surface of a vessel to scan the counts, which pass through the molten foamed glass at a range of depths. In certain other embodiments, a single EM source may be used with a plurality of EM detectors stacked vertically. In yet other embodiments, multiple pairing of EM sources and EM detectors may be used at different locations. In still other embodiments a single EM source and a single EM detector may be used to measure the molten foamed glass density at a single point with some ability to adjust the EM source and EM detector vertically if a new depth within the vessel becomes pertinent. Based on the path the EM wave must travel, the glass density gradient within the path, the amount of radiation detected by the EM detector is a function of both the glass level as well as the range of densities of the molten foamed glass in the path of the radiation. If both the EM source and the EM detector are stationary, then measuring the glass level can provide an indication regarding how much of a change in detection could be due to a change in effective glass level, and how much is due to a change in glass density.

Figure 9:
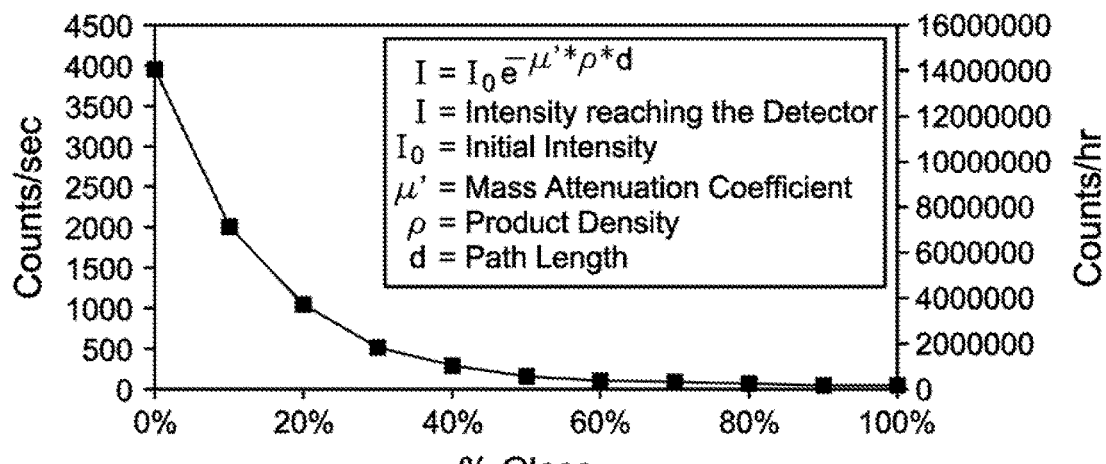
FIG. 9 is a representative graph of counts/second received at an EM detector vs. "percent glass"

The EM detector returns the amount of radiation detected per unit of time. The output is a relationship between radiation count and time. This radiation count may then be converted to a glass density as a function of the vertical position of the EM source and EM detector. The EM sensor can be calibrated by measuring the detectable radiation with the vessel empty, as well as with the vessel filled above the highest EM detector. Molten glass comprising very few bubbles will result in greater absorption than molten foamed glass. The resulting curve may also be used to estimate glass level in the vessel. Equation (1) may be used to approximate glass density as a function of radiation intensity, and FIG. 9 is a graphical representation of a sample curve with an assumed initial intensity of 4000 counts per second and a path length of twenty-three inches.

$$I = I_0 e^{-\mu'*\rho*d} \quad (1)$$

where:
 I=intensity reaching the EM detector
 $I_0$=initial intensity
 $\mu'$=mass attenuation coefficient
 $\rho$=product density
 d=path length As noted previously, the EM source may be wave or particle based, and any type may be used as long they may be used safely and within regulations imposed by local and/or national authorities. For commercial purposes, gamma radiation sources may be used, such as Cobalt-60 and Cesium-137 (also referred to as Caesium-137). The following discussion is taken from *Gamma Irradiators for Radiation Processing*, a publication of the International Atomic Energy Agency (IAEA), Vienna, Austria. Within the electromagnetic radiation spectrum, gamma radiation is located near the high energy end along with X rays. The energy associated with gamma radiation (for example, gamma rays emitted by cobalt-60) is high enough to break the molecular bonds and ionize atoms, but not high enough to affect structure of the atomic nucleus (avoiding induction of radioactivity). Gamma radiation may, therefore, modify chemical, physical or biological properties of the irradiated material/product; however, the irradiated product does not become radioactive. Radiation with such high energy is referred to as ionizing radiation. All radiation processing is performed with ionizing radiation, which includes—besides gamma radiation—high energy electrons (generally >80 keV) and X rays generated from high energy electrons (e.g., 5-10 MeV).

Cobalt-60 and caesium-137 are the most suitable gamma radiation sources for radiation processing because of the relatively high energy of their gamma rays and fairly long half-life (5.27 years for cobalt-60 and 30.1 years for caesium-137). However, the use of caesium-137 has been limited to small self-contained, dry-storage irradiators, used primarily for the irradiation of blood and for insect sterilization. The radionuclide cobalt-60 (Co-60 or 60Co27) is the most commonly used source of gamma radiation for radiation technology, both for industrial and medical purposes, and is used in most embodiments of the present disclosure. Production of radioactive cobalt starts with natural cobalt (metal), which is an element with 100% abundance of the stable isotope cobalt-59. Cobalt-rich ore is rare and this metal makes up only about 0.001% of the earth's crust. Slugs (small cylinders) or pellets made out of 99.9% pure cobalt sintered powder and generally welded in Zircaloy capsules are placed in a nuclear power reactor, where they stay for a limited period (about 18-24 months) depending on the neutron flux at the location. While in the reactor, a cobalt-59 atom absorbs a neutron and is converted into a cobalt-60 atom. During the two years in the reactor, a small percentage of the atoms in the cobalt slug are converted into cobalt-60 atoms. Specific activity is usually limited to about 120 Ci/g of cobalt (about $4 \times 10^{12}$ Bq/g). After irradiation, the capsules containing the cobalt slugs are further encapsulated in corrosion resistant stainless steel to finally produce the finished "source pencils" in a form such that gamma radiation can come through but not the radioactive material (cobalt-60) itself.

As disclosed in the IAEA bulletin mentioned above, the required source geometry is obtained by loading these source pencils into predetermined positions in "source modules", and distributing these modules over the "source rack" of the industrial irradiator. It should be noted that the present disclosure is not limited to use of "source pencils", "source modules", and "source racks" as described by the IAEA, but this terminology will be adhered to herein for convenience. A non-limiting variety of possible configurations and embodiments of EM sources, EM source modules, EM source racks, and EM detectors will be described herein.

Cobalt-60 (60Co27) decays (disintegrates) into a stable (non-radioactive) nickel isotope (60Ni28) principally emitting one negative beta particle (of maximum energy 0.313 MeV) with a half-life of about 5.27 years. Nickel-60 thus produced is in an excited state, and it immediately emits two photons of energy 1.17 and 1.33 MeV in succession to reach its stable state. These two gamma ray photons are responsible for radiation processing in the cobalt-60 gamma irradiators. With the decay of every cobalt-60 atom, the strength or the radioactivity level of the cobalt source is decreasing, such that the decrease amounts to 50% in about 5.27 years, or about 12% in one year. According to the IAEA bulletin mentioned herein, additional pencils of cobalt-60 are added periodically to the source rack to maintain the required capacity of the irradiator; however, in the practice of the methods and systems of the present disclosure, this may not be necessary, if calculation scan be made to account for this decrease in source strength. Cobalt-60 pencils are eventually removed from the irradiator at the end of their useful life, which is typically 20 years. Generally they are returned to the supplier for re-use, recycling or disposal. In about 50 years, 99.9% of cobalt-60 would decay into non-radioactive nickel.

The EM source may be sized appropriately depending upon the expected attenuation between the EM source and the EM detector due to distance, vessel wall thickness, vessel wall density, width of the molten foamed glass pool or stream being analyzed, molten foamed glass density, and EM detector size being utilized. Provided this information, a vendor supplying the EM source and EM detector should be able to size the EM source appropriately without undue experimentation. "Radiation absorbed dose" is the measure of absorbed radiation energy, and is defined as the radiation energy (in joule, J) absorbed by unit mass (in kilogram, kg) of the product; it is measured in units of gray (Gy). Thus, 1 gray (Gy)=1 J/kg. "Dose rate" is the dose given in unit time and is determined by the activity of the radiation source and the irradiation geometry. It is measured in, for example kGy/h or Gy/s. According to the IAEA bulletin, dose rate in a research irradiator can be up to 20 kGy/h, and in "an industrial facility" (for example, with 3 MCi of cobalt-60), it can be as high as 100 kGy/h near the source, but on the average it is around 10 kGy/h. Those skilled in the art of supplying EM sources and EM detectors will understand the need to also take dose rate into account in selecting an appropriately sized EM source(s) and shielding for any given measurement. Dose rate may vary as glass density varies (over time and/or system position). In methods and systems of the present disclosure, the dose rate may vary depending upon the glass density. The dose rate may depend on EM source type, EM source size, vessel wall thickness, vessel wall density, vessel internal width, glass density, total path length, and shielding design. For example, for EM sources positioned near the bottom of a downstream apparatus and projecting their radiation through mostly molten glass with few bubbles, the dose rate may be larger than for EM sources near the bubble layer, potentially necessitating additional shielding. "Radioactivity level" is the strength (or power) of a radiation source, which is defined as the number of disintegrations of radioactive nuclides per second. The special name of the SI unit is becquerel (Bq). However, this is a very small amount of activity, and traditionally activity is measured in units of curie (Ci). Thus, 1 becquerel (Bq)=1 dis/s=1 s$^{-1}$, and 1 curie (Ci)=3.7×10$^{10}$ Bq. As with does rate, the radioactivity level may vary from EM source to EM source. For example, for EM sources positioned near the bottom of a downstream apparatus and projecting their radiation through mostly molten glass with few bubbles, the radiation level may need to be larger than for EM sources near the bubble layer. If the glass density is expected to range as low as 0 g/cc at certain times or in certain scan location, the certain systems and methods of the present disclosure may be engineered such that a particular EM source will not overpower and/or damage the EM detector due to excessive signal strength. If the low molten foamed glass density is expected only in certain locations, then additional shielding, such as steel or lead plates, may be employed in those locations to reduce the maximum signal strength reaching the EM detector. Similarly, engineering controls may be necessary to keep the maximum dose rate within the limits required by pertinent regulatory agencies. Given the known of variables within the system design and operation, appropriate shielding for each individual system will be readily apparent to those skilled in the art with minimal experimentation.

The glass density, expected air fraction range, and the refractory which normally (but not always) makes up the vessel walls, will all attenuate the EM source signal. In certain embodiments the location of the EM source and EM detector may be carefully selected to ensure there is sufficient signal strength at the EM detector to achieve the measurement sensitivity desired.

In certain embodiments, a lack of EM source strength may be compensated for by performing longer measurement times. For example, in certain embodiments, the strength may be monitored in counts per minute or counts per hour, instead of counts per second. Also, in certain embodiments background radiation may be more accurately accounted for by having the traversing system (frame) perform regular background radiation checks or calibrations. This is possible by either having the system move to setting within the system where virtually none of the radiation from the EM source can reach the EM detector. Some examples of how this may be accomplished include, but are not limited to, misaligning the EM source and EM detector, closing an EM source shutter, moving the EM source and EM detector to a location where there is material of sufficient volume and density to virtually completely attenuate the EM source, or some combination thereof.

"Submerged" as used herein means that combustion gases emanate from a combustion burner exit that is under the level of the molten glass, and "non-submerged" means that combustion gases do not emanate from combustion burner exits under the level of molten glass, whether in the SCM or downstream apparatus. Both submerged and non-submerged burners may be roof-mounted, floor-mounted, wall-mounted, or any combination thereof (for example, two floor mounted burners and one wall mounted burner). "SC" as used herein means "submerged combustion" unless otherwise specifically noted, and "SCM" means submerged combustion melter unless otherwise specifically noted.

The terms "foam" and "foamy" include froths, spume, suds, heads, fluffs, fizzes, lathers, effervesces, layer and the like. The term "bubble" means a thin, shaped, gas-filled film of molten glass. The shape may be spherical, hemispherical, rectangular, polyhedral, ovoid, and the like. The gas or "bubble atmosphere" in the gas-filled SC bubbles may comprise oxygen or other oxidants, nitrogen, combustion products (including but not limited to, carbon dioxide, carbon monoxide, $NO_x$, $SO_x$, $H_2S$, and water), reaction products of glass-forming ingredients (for example, but not limited to, sand (primarily $SiO_2$), clay, limestone (primarily $CaCO_3$), burnt dolomitic lime, borax and boric acid, and the like. Bubbles may include solids particles, for example soot particles, either in the film, the gas inside the film, or both. The term "glass foam" means foam where the liquid film comprises molten glass. "Glass level" means the distance measured from the bottom of a downstream apparatus to the upper liquid level of the molten glass, and "foam level" means the distance measured from the top of the atmosphere above the foam layer to the upper surface of the foam layer. "Foam height" (equivalent to foam thickness) is the distance measured between the glass level and foam level.

As used herein the term "combustion" means deflagration-type combustion unless other types of combustion are specifically noted, such as detonation-type combustion. Deflagration is sub-sonic combustion that usually propagates through thermal conductivity; hot burning material heats the next layer of cold material and ignites it. Detonation is supersonic and primarily propagates through shock. As used herein the terms "combustion gases" and "combustion products" means substantially gaseous mixtures of combusted fuel, any excess oxidant, and combustion products, such as oxides of carbon (such as carbon monoxide, carbon dioxide), oxides of nitrogen, oxides of sulfur, and water, whether from deflagration, detonation, or combination thereof. Combustion products may include liquids and solids, for example soot and unburned or non-combusted fuels.

"Oxidant" as used herein includes air and gases having the same molar concentrations of oxygen and nitrogen as air (synthetic air), oxygen-enriched air (air having oxygen concentration greater than 21 mole percent), and "pure" oxygen, such as industrial grade oxygen, food grade oxygen, and cryogenic oxygen. Oxygen-enriched air may have 50 mole percent or more oxygen, and in certain embodiments may be 90 mole percent or more oxygen.

The term "fuel", according to this disclosure, means a combustible composition comprising a major portion of, for example, methane, natural gas, liquefied natural gas, propane, hydrogen, steam-reformed natural gas, atomized hydrocarbon oil, combustible powders and other flowable solids (for example coal powders, carbon black, soot, and the like), and the like. Fuels useful in the disclosure may comprise minor amounts of non-fuels therein, including oxidants, for purposes such as premixing the fuel with the oxidant, or atomizing liquid or particulate fuels. As used herein the term "fuel" includes gaseous fuels, liquid fuels, flowable solids, such as powdered carbon or particulate material, waste materials, slurries, and mixtures or other combinations thereof.

The sources of oxidant and fuel may be one or more conduits, pipelines, storage facility, cylinders, or, in embodiments where the oxidant is air, ambient air. Oxygen-enriched oxidants may be supplied from a pipeline, cylinder, storage facility, cryogenic air separation unit, membrane permeation separator, or adsorption unit such as a vacuum swing adsorption unit.

The term "downstream apparatus" means a container, channel or conduit defined at least by a floor and a wall structure extending upwards from the floor to form a space in which molten glass may be present, whether flowing or not. In certain embodiments the downstream apparatus will include a roof and a wall structure connecting the floor and roof. The downstream apparatus may have any operable cross-sectional shape (for example, but not limited to, rectangular, oval, circular, trapezoidal, hexagonal, and the like) and any flow path shape (for example, but not limited to, straight, zigzag, curved, and combinations thereof). In certain systems and methods the downstream apparatus may be a flow channel selected from the group consisting of a conditioning channel, a distribution channel, and a forehearth.

Downstream apparatus, frames and associated structures, as well as conduits used in burners and devices for delivery of compositions useful in systems and methods of the present disclosure may be comprised of metal, ceramic, ceramic-lined metal, or combination thereof. Suitable metals include stainless steels, for example, but not limited to, 306 and 316 steel, as well as titanium alloys, aluminum alloys, and the like. Suitable materials for the glass-contact refractory, which may be present in SC melters and flow channels, and refractory burner blocks (if used), include fused zirconia ($ZrO_2$), fused cast AZS (alumina-zirconia-silica), rebonded AZS, or fused cast alumina ($Al_2O_3$). The particular system and method, downstream apparatus, frame and associated structures and radiation shielding, burner geometry, type of glass to be produced and degree of foaming, industry standards such as promulgated by the American Society of Testing Materials (ASTM), American National Standards Institute (ANSI), International Standards Organization (ISO), and the like, and local and national laws and regulations may all dictate the choice of a particular material, among other parameters.

Certain submerged and non-submerged combustion burners, certain components in and/or protruding through one or more of the floor, roof, and sidewall structure configured to heat or maintaining temperature of the foamed glass, frames and associated shielding apparatus for supporting EM sources and detectors, and the like, useful in systems and methods of this disclosure may be fluid-cooled, and in the case of burners may include first and second (or more) concentric conduits. In the case of burners, the first conduit may be fluidly connected at one end to a source of fuel, the second conduit may be fluidly connected to a source of oxidant, and a third substantially concentric conduit may connect to a source of cooling fluid.

Certain systems of this disclosure may comprise one or more non-submerged burners. Suitable non-submerged combustion burners may comprise a fuel inlet conduit having an exit nozzle, the conduit and nozzle inserted into a cavity of a ceramic burner block, the ceramic burner block in turn inserted into either the roof or the wall structure, or both the roof and wall structure of the downstream apparatus.

In certain systems, one or more burners may be adjustable with respect to direction of flow of the combustion products. Adjustment may be via automatic, semi-automatic, or manual control. Certain system embodiments may comprise a burner mount that mounts the burner in the wall structure, roof, or floor of the downstream apparatus comprising a refractory, or refractory-lined ball joint or ball turret. Other burner mounts may comprise rails mounted in slots in the wall or roof. In yet other embodiments the burners may be mounted outside of the downstream apparatus, on supports that allow adjustment of the combustion products flow direction. Useable supports include those comprising ball joints, cradles, rails, and the like.

In certain systems and methods of the present disclosure, the downstream apparatus may comprise a flow channel comprising a series of sections, and may comprise one or more skimmers and/or impingement (high momentum) burners, such as described in assignee's U.S. Pat. Nos. 9,021,838, and 8,707,739. Certain systems and methods of the present disclosure may utilize measurement and control schemes such as described in assignee's application Ser. No. 13/493,219, filed Jun. 11, 2012, now U.S. Pat. No. 9,096,453, and/or feed batch densification systems and methods as described in assignee's co-pending application Ser. No. 13/540,704, filed Jul. 3, 2012. Certain systems and methods of the present disclosure may utilize one or more retractable devices for delivery of treating compositions such as disclosed in assignee's U.S. Pat. No. 8,973,405. Certain systems and methods of the present disclosure may utilize one or more nozzles for delivery of treating compositions such as disclosed in assignee's co-pending application Ser. No. 13/644,058, filed Oct. 3, 2012, and/or may utilize one or more foam destruction devices as described in assignee's application Ser. No. 13/644,104, filed Oct. 3, 2012, now U.S. Pat. No. 9,096,452.

Certain systems and methods of this disclosure may be controlled by one or more controllers. For example, determination of molten foamed glass density gradient may be used to control one or more burners in the downstream apparatus and/or melter, level in a melter, feed rate to a melter, discharge rate of molten foamed glass from a melter, and other parameters. Burner (flame) temperature may be controlled by monitoring one or more parameters selected from velocity of the fuel, velocity of the primary oxidant, mass and/or volume flow rate of the fuel, mass and/or volume flow rate of the primary oxidant, energy content of the fuel, temperature of the fuel as it enters the burner, temperature of the primary oxidant as it enters the burner, temperature of the effluent, pressure of the primary oxidant entering the burner, humidity of the oxidant, burner geometry, combustion ratio, and combinations thereof. Certain systems and methods of this disclosure may also use determined density gradient of molten foamed glass in the downstream apparatus to control feed rate of batch or other feed materials, such as glass batch, cullet, mat or wound roving and treatment compositions, to a melter; mass of feed to a melter, and the like. Exemplary systems and methods of the disclosure may comprise a controller which receives one or more input parameters selected from temperature of melt in a melter, density gradient in the downstream apparatus, composition of bubbles and/or foam, height of foam layer, glass level, foam level, and combinations thereof, and may employ a control algorithm to control combustion temperature, flow rate and/or composition of compositions to control foam decay rate and/or glass foam bubble size, and other output parameters based on one or more of these input parameters.

Specific non-limiting system and method embodiments in accordance with the present disclosure will now be presented in conjunction with the attached drawing figures. The same numerals are used for the same or similar features in the various figures. In the views illustrated in the drawing figures, it will be understood in each case that the figures are schematic in nature, and certain conventional features may not be illustrated in all embodiments in order to illustrate more clearly the key features of each embodiment. The geometry of the downstream apparatus is illustrated generally the same in the various embodiments, but that of course is not necessary. Certain systems and methods may be described as comprising an SCM and one or more downstream apparatus receiving flow of molten glass and foam from the SCM.

FIGS. 1, 2, 3, 4, 6, 7, and 8 are schematic transverse cross-sectional views of seven non-limiting alternative system embodiments in accordance with the present disclosure. While most embodiments illustrate EM sensors on downstream apparatus, this is merely for convenience, it being understood that EM sensors may also or alternatively be positioned on the melters. FIG. 1 is a schematic transverse cross-section of embodiment 100. Downstream apparatus 40 includes a roof 4, a floor 6, and a sidewall structure 8 connecting roof 4 and floor 6. A first portion of sidewall structure 8 and floor 6 define a first space 10 containing molten foamed glass 14 having a plurality of entrained bubbles 15. A foam layer 16 floats on top of molten foamed glass 14, comprised of foam layer bubbles 17. A second portion of sidewall structure 8 and roof 4 defines a second space 12 for containing an atmosphere 18 above foam layer 16. In certain embodiments, roof 4 and foam layer 16 may not be present, or may not be present in the entire downstream apparatus 40. These features are generally also present in embodiments 200, 300, 400, 500, 600, 700, and 800 (FIGS. 2-8, respectively), and will not be repeated for each embodiment. However, as will be understood, the shape of the roof, floor, and sidewall structure of downstream apparatus 40, the location of the level of molten foamed glass 14, the amount of entrained bubbles 15, and amount of bubbles 17 in foam layer 16, size of first and second spaces 10, 12, may vary widely.

Referring again to FIG. 1, a frame comprising frame portions 30A, 30B extend generally vertically from a plant floor 1 or other support structure up to points along portion 8A, 8B of external surface of sidewall structure 8. Frame portion 30A supports at least one EM source 32 of an EM sensor, while frame portion 30B supports at least one EM detector 30B of the EM detector. The height of frame portions 30A, 30B may be less than, equal to, or greater than the height of roof 4, while the horizontal length of frame portions 30A, 30B depends on the features of each embodiment, as will become apparent reading further herein. For example, if there is only one stationary EM source 32 and one stationary EM detector 34, as in embodiment 100, then frame portions 30A, 30B may simply be posts. Appropriate radiation shielding will also be required, but for the purposes of this disclosure, it is assumed the amount and position of shielding will be dictated by government laws, regulations, and/or industry standards, and so is not illustrated in the drawing figures. Furthermore, although a gap is illustrated between EM source 32 and first portion 8A of sidewall structure 8, as well as between EM detector 34 and second portion 8B of sidewall structure 8, this may not be so in every embodiment, an is intended to indicate that in certain embodiments these gaps may or may not exist.

Figure 10:
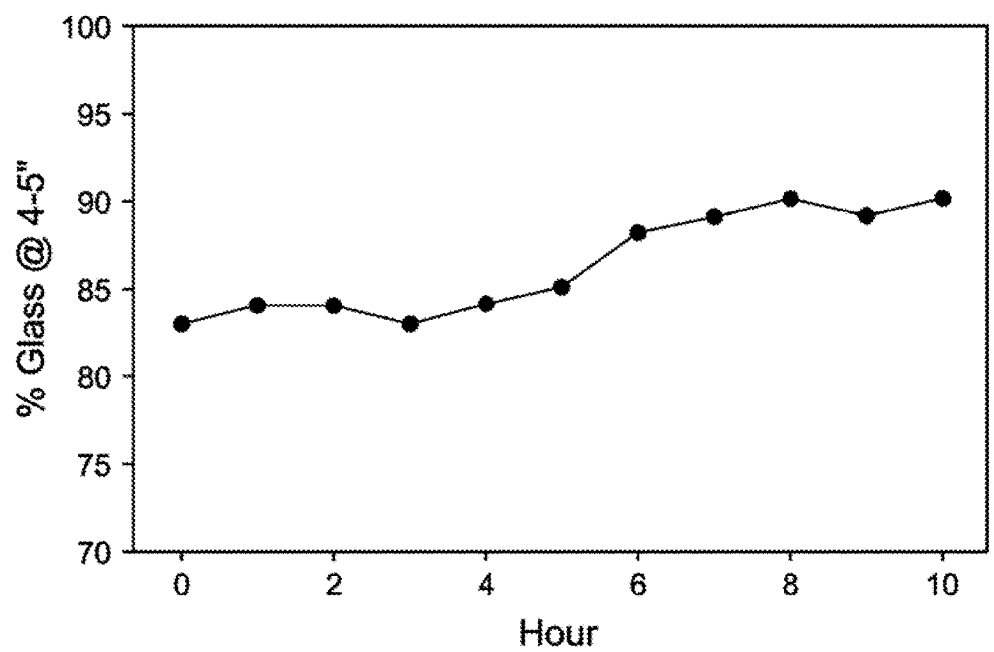

As mentioned, embodiment 100 describes an embodiment where there is only one stationary EM source 32 and one stationary EM detector 34. These may for example be positioned 4-5 inches above floor 6. FIG. 10 represents how the percentage of glass at that depth or elevation in downstream apparatus 40 may appear over the passage of 10 hours. This is only a hypothetical example, but based on experience.

Referring now to FIGS. 2-8, further embodiments and features of systems and methods of the present disclosure may be noted. Embodiment 200 illustrated schematically in FIG. 2 features a frame 30 comprising two generally vertical portions 30A, 30B, connected by a generally horizontal portion 30C, with frame portions 30A, 30B supporting EM source 32 and EM detector 34, respectively. Optionally or alternatively, one or more EM source 32A may be positioned on generally horizontal portion 30C, and one or more EM detectors below floor 6 of downstream apparatus 40. Sections 30A, 3B, and 30C may extend the entire length of sidewall structure 8, or only a portion thereof. EM source 32 and EM detector 34 may or may not be stationary in this embodiment. Embodiment 300 illustrated schematically in FIG. 3 features a frame 30 having two generally vertical sections 30A, 30B supported from above by a third portion 30C that may be suspended from an overhead lift or crane (not illustrated), and that may move horizontally and vertically for example upon one or more rails. Vertical portions 30A and 30B may be posts or I-beams, for example, and may be moved along sidewall portions 8A, 8B as desired, or frame portions 30A, 30B may be moveable only horizontally while EM source 32 and EM detector 34 are moved vertically, for example in slots, rollers, cams, wheels, or other mechanical feature built into frame portions 30A, 30B. Many other variations are possible. In certain embodiments, a plurality of EM sources and EM detectors may be arranged on stationary frame portions 30A, 30B, and one or more of the EM sources and EM detector adapted to move as desired.

Figure 4:
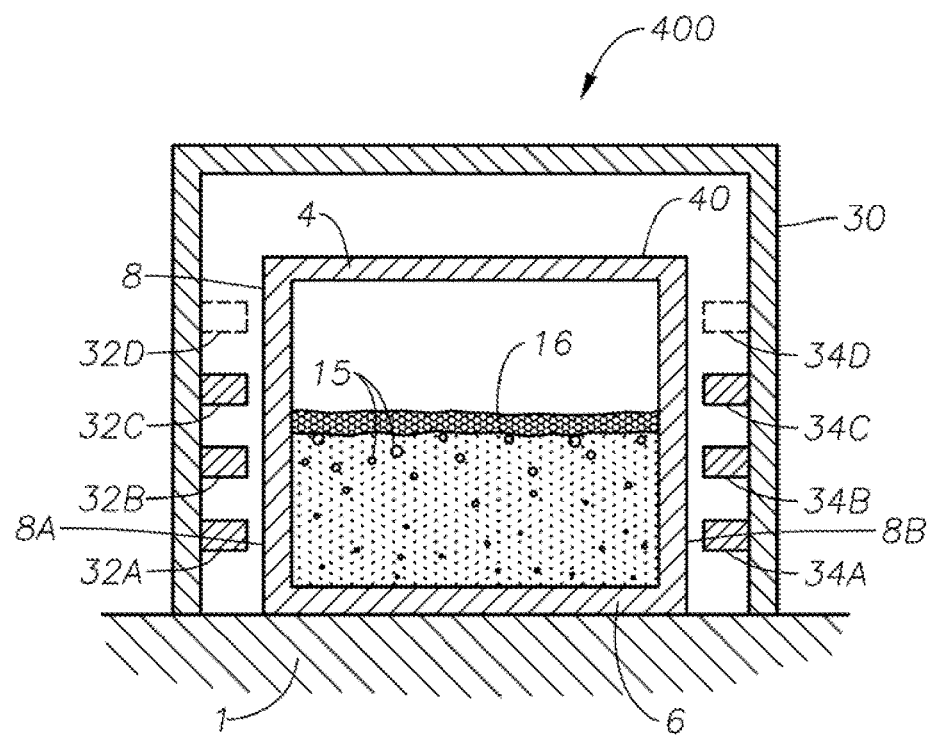

FIG. 4 illustrates schematically another embodiment 400, which features a frame similar to that illustrated in embodiment 200 supporting at least three EM sources 32A, 32B, 32C, and at least three EM detectors 34A, 34B, and 34C. EM source 32A may pair with any of EM detectors 34A, 34B, and 34C to form an EM sensor pair. Another EM source 32D is illustrated schematically in phantom, indicating that it is merely optional. Optional EM source 34D may be associated with a corresponding optional EM detector 34D, or with one of EM detectors 34A, 34B, or 34C. If all of EM sources 32A-D are stationary and paired with their horizontally opposed, stationary EM detectors 34A-D, four informational graphs such as depicted in FIG. 9 would be available to the operator, for four different elevations or depths within downstream apparatus 40 or other vessel (such as a melter), thus providing more information on density gradient than for example the arrangement in embodiment 100. In embodiments such as embodiment 400 illustrated schematically in FIG. 4, frame 30 may be stationary or moveable. If frame 30 is stationary, one or more EM sources and/or EM detectors may be moveable horizontally, vertically, or both.

Figure 5:
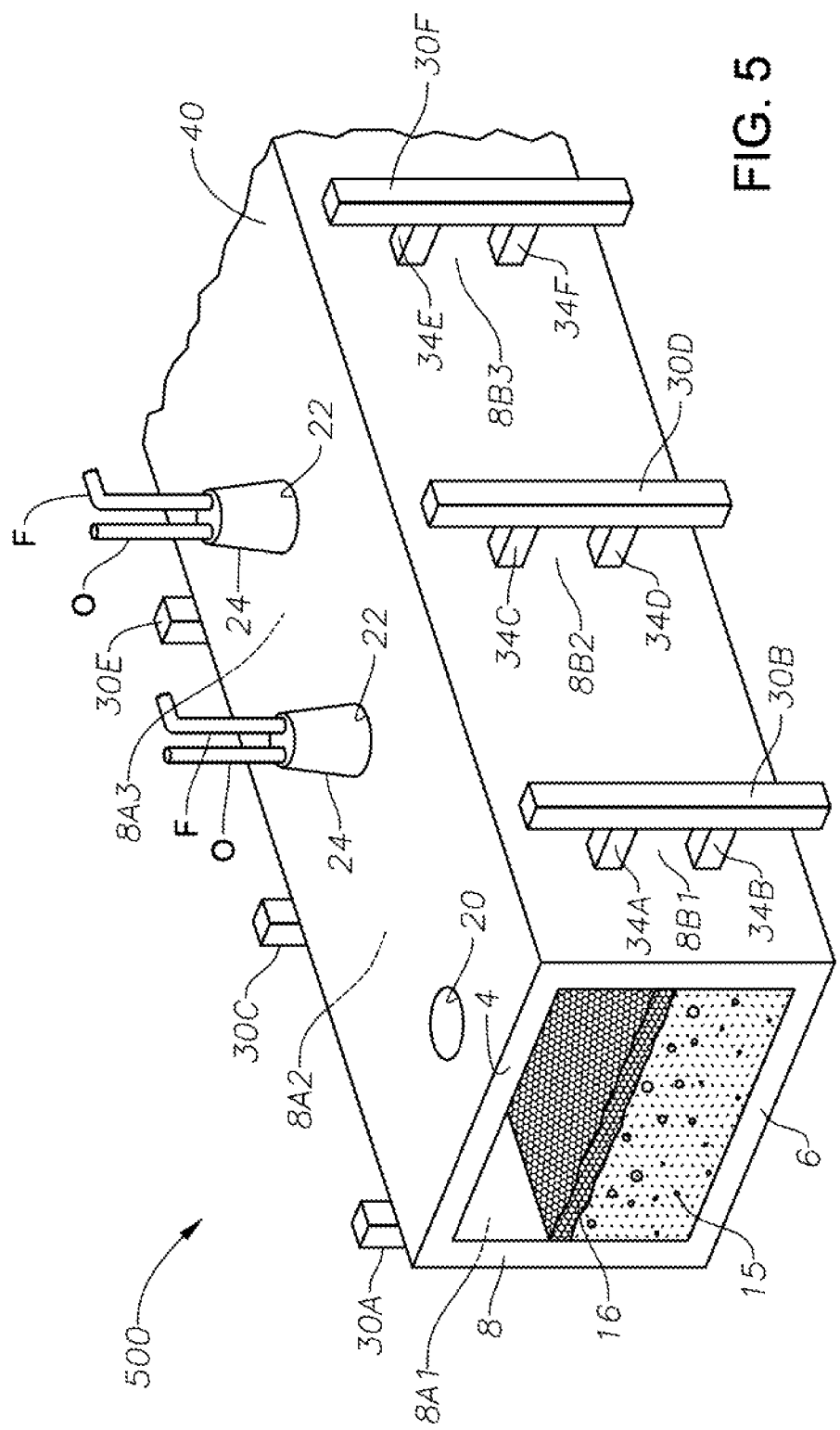
FIG. 5 is a schematic perspective view of another system embodiment in accordance with the present disclosure.

FIG. 5 illustrates schematically a perspective view of another downstream apparatus system and method embodiment 500 in accordance with the present disclosure. Embodiment 500 features six or more generally vertical frame portions or members 30A, 30B, 30C, 30D, 30E, and 30F. Frame portions 30A, 30C, and 30E each support two vertically spaced EM sources that are out of view in FIG. 5, while frame portions 30B, 30D, and 30F each support two vertically spaced EM detectors. Frame portion 30A supports EM sources 32A, 32B (out of view) that emit initial radiation toward and through sidewall portion 8A1. Similarly, frame portion 30C supports EM sources 32C, 32D (out of view) that emit initial radiation toward and through sidewall portion 8A2, and frame portion 30E supports EM sources 32E, 32F (out of view) that emit initial radiation toward and through sidewall portion 8A3. Frame portion 30B supports EM detectors 34A, 34B, which detect attenuated EM radiation through sidewall section 8B1. Similarly, frame portion 30D supports EM detectors 34C, 34D, which detect attenuated EM radiation through sidewall section 8B2, and frame portion 30F supports EM detectors 34E, 34F, which detect attenuated EM radiation through sidewall section 8B3.

Still referring to FIG. 5, the downstream apparatus 40 in embodiment 500 includes an inlet aperture 20 for molten foamed glass to flow into downstream apparatus 40 from a melter, such as an SCM, as well as two apertures 22 for burners 24, which may be oxy/fuel burners fed with oxygen-enriched oxidant "O" and fuel "F". One or both burners 24 may either be used for heating, or may be foam impingement burners. Embodiment 500 affords an operator very good information on gradient density of the molten foamed glass both in the vertical as well as horizontal directions.

Figure 6:
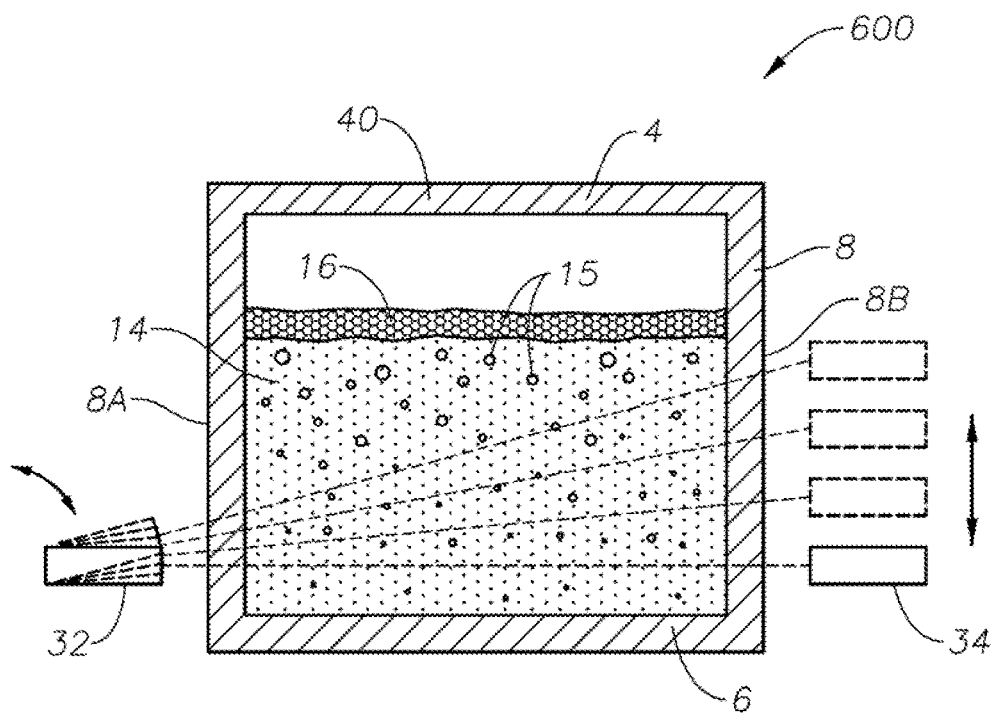
Figure 7:
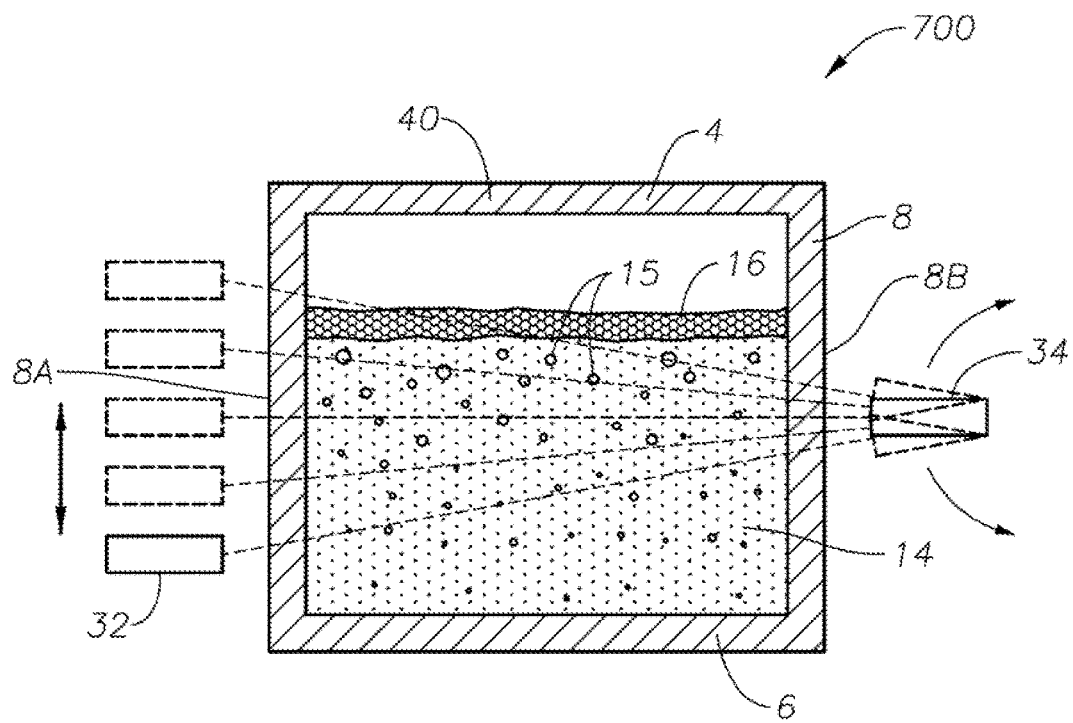
Figure 11:
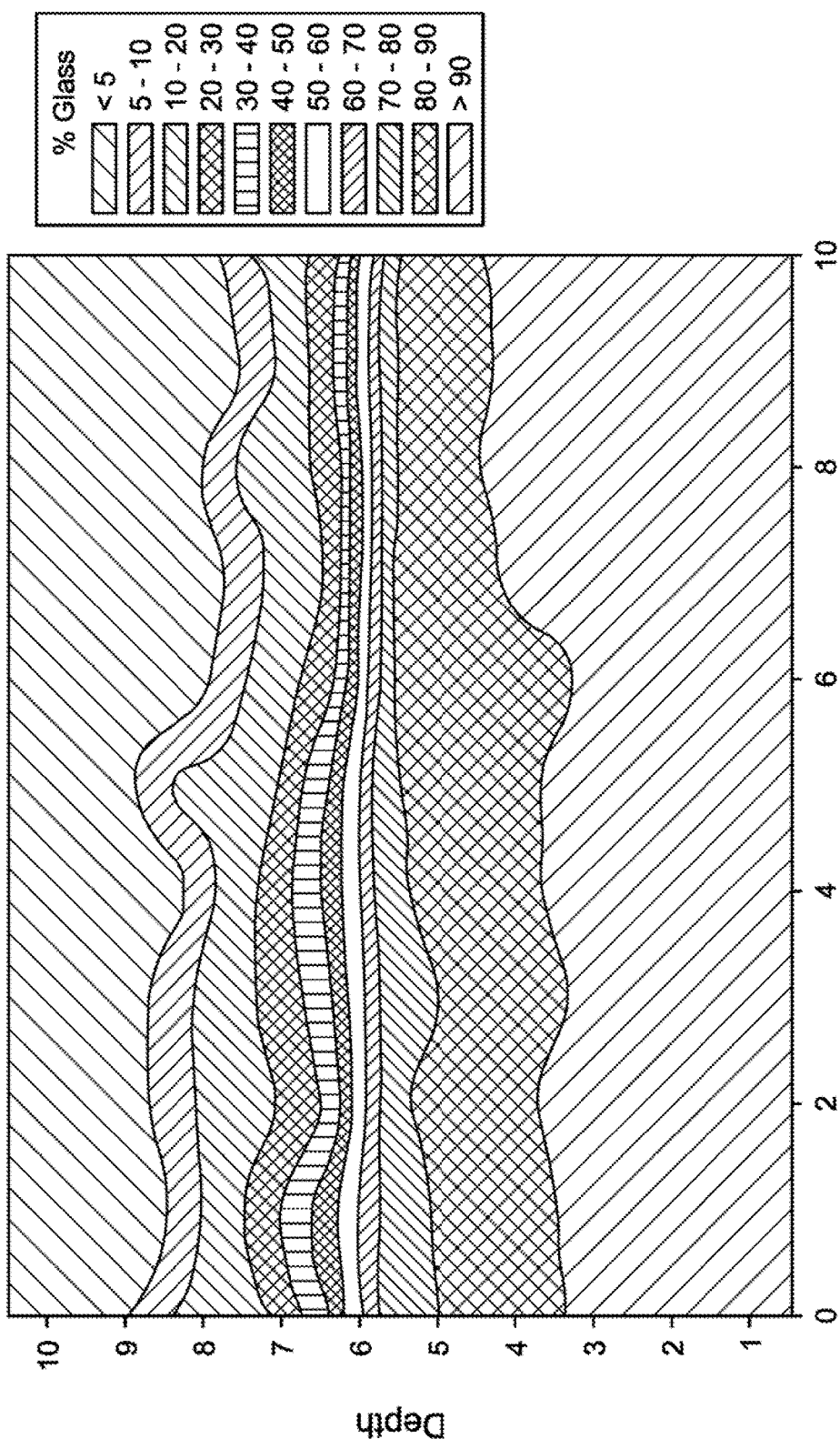
FIG. 11 is a graph of "depth" in an apparatus downstream of a submerged combustion melter vs. time in hours for an embodiment where both EM source and detector are moving during an operation to determine density gradient of foamed glass.

FIGS. 6 and 7 illustrate schematically two other system and method embodiments 600 and 700 in accordance with the present disclosure. Embodiments 600 and 700 allow qualitative and quantitative information to be obtained regarding the density gradient of molten foamed glass 14 and foam layer 16, if present, as well as position of the top of the foam layer. Embodiment 600 features a stationary but pivotable EM source 32 near sidewall portion 8A, the pivot action of EM source 32 represented by the phantom boxes and the double-headed curved arrow near EM source 32. Although only one EM source 32 is illustrated, there could be more than one EM source 32A, 32B, etc. spaced horizontally along sidewall 8A, at the same or different heights. A frame portion or member, not illustrated for clarity, would support EM source 32. Also illustrated is a vertically moveable EM detector 34, moveable vertically along sidewall portion 8B as indicated by the three phantom boxes and the double-headed straight arrow by virtue of sliding or rolling in a groove or other appropriate mechanical feature in a frame portion, not illustrated for clarity. Alternatively, there could be a plurality of EM detectors 34A, 34B, etc., spaced vertically along sidewall portion 8B, positioned to intercept attenuated radiation from one pivotable EM source 32. Embodiment 700 features a vertically moveable EM source 32, as indicated by the four phantom boxes and the double-headed straight arrow by virtue of sliding or rolling in a groove or other appropriate mechanical feature in a frame portion, not illustrated for clarity, while a single stationary but pivotable EM detector 34 near sidewall portion 8B, the pivot action of EM detector 34 represented by the phantom boxes and the single-headed curved arrows near EM detector 34. Although only one EM detector 34 is illustrated, there could be more than one EM detector 34A, 34B, etc. spaced horizontally along sidewall portion 8B, at the same or different heights. FIG. 11 shows graphically a possible view of depth vs. time for a system and method incorporating moveable EM sources and/or moveable EM detectors. Certain systems would not perform a continuous scan, and thus the visualization of FIG. 11 may require interpolation between measured data points.

Figure 6A:
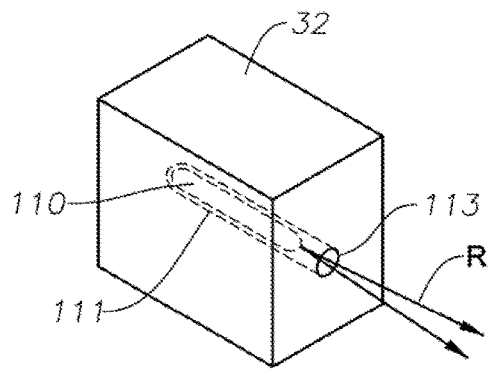
Figure 6B:
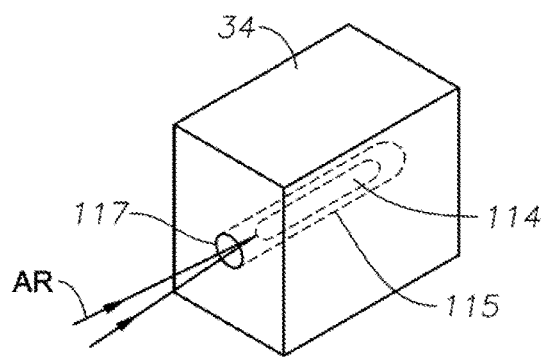
Figure 7A:
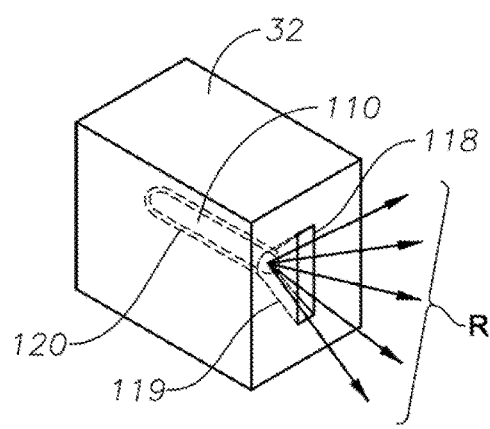
Figure 7B:
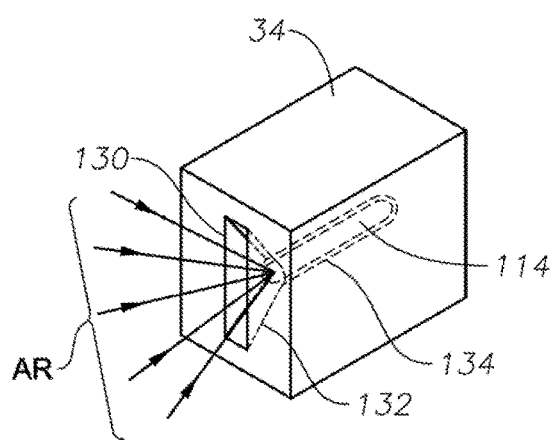

FIGS. 6A, 6B, 7A, and 7B are schematic perspective views, not to scale, of possible alternative EM sources and EM detectors useful in systems and methods of this disclosure. FIG. 6A illustrates schematically an EM source 32, generally including lead (Pb) or other shielding surrounding a pencil-shaped source element 110 contained in a slightly larger pencil-shaped source cavity 111. EM source waves, denoted at "R", emanate from an orifice 113 in a narrow, circular band. FIG. 6B illustrates schematically a similar arrangement for EM detector 34, which may also comprise a lead-shielded body, a detector cavity 115 housing an EM detector element 114. Attenuated EM waves, denoted "AR", are illustrated schematically as entering through an orifice 117. Orifice 117 may be slightly large than orifice 113 in order to ensure capturing "AR" waves. EM source 32 and detector 34 illustrated schematically in FIGS. 6A and 6B may be used in the systems illustrated schematically in FIGS. 6 and 7, where either the EM source 32 (FIG. 6) or EM detector 34 (FIG. 7) pivots. FIGS. 7A and 7B illustrate an alternative arrangement, where instead of pivoting, EM source 32 comprises a vertical slot aperture 118, a narrow cone cavity portion 119, and a pencil-shaped cavity 120 holding an EM source element 110. Similarly, EM detector 34 illustrated schematically in FIG. 7B comprises a vertical slot aperture 130, a narrow conical cavity 132, and a pencil-shaped cavity 134 supporting an EM detector element 114. Radiation "R" emanating from vertical slot 118 may then be detected at detector element 114 as attenuated radiation "AR" through vertical slot aperture 130. Vertical slot aperture 130 in EM detector 34 may be slightly large than vertical slot aperture 118 in EM source 32 in order to ensure capturing "AR" waves. In the embodiments illustrated schematically in FIGS. 7A and 7B, there would be less or no need to pivot EM source 32 as in embodiment 600 illustrated schematically in FIG. 6, or pivot EM detector 34 as illustrated schematically in embodiment 700 of FIG. 7.

Figure 8:
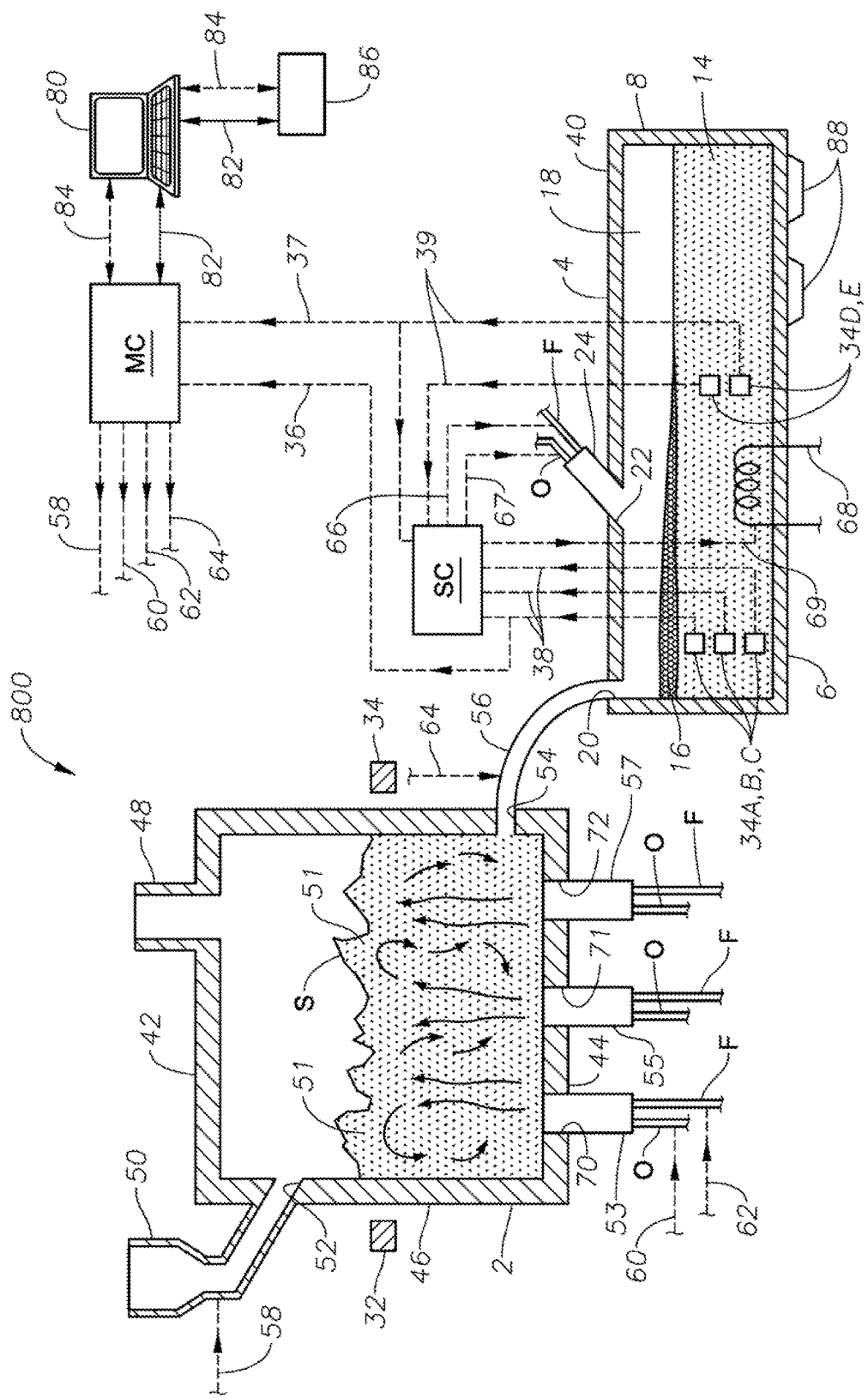

FIG. 8 illustrates schematically an embodiment 800 comprising an SCM 2, the SCM including in this embodiment an SCM roof 42, SCM floor 44, and SCM sidewall structure 46 connecting roof 42 and floor 44, with roof 42 including an opening for a stack 48. SCM 2 produces a turbulent molten foamed glass 51 from one or more vitrifiable feed materials, for example glass batch fed from a feeder 50 through an inlet port 52. SCM 2 includes one or more SC burners 53, 55, and 57, protruding through respective apertures 70, 71, and 72 in SC floor 44, and in certain embodiments one or more SC burners 53, 55, and 57 may be oxy/fuel burners combusting fuel "F" with an oxygen-enriched oxidant "O". Turbulence created by SC burners 53, 55, and 57 in molten foamed glass 51 is indicated schematically by curved flow lines, single-headed arrows, and rolling surface "S". While the exits of SC burners may be flush with SC floor 44, SC burner 55 is illustrated as protruding slightly into SCM 2. SC burners 53, 55, and 57 may have one or more companion burners spaced transversely therefrom (not shown). SC burners may be placed randomly or non-randomly to protrude through floor 44 and/or sidewall structure 46. SCM 2 feeds at least a portion of molten foamed glass 51 to a downstream apparatus 40 through an SCM exit port 54 and SCM exit structure 56. The melter may include one or more stationary or movable EM sources 32, and one or more stationary or movable EM detectors 34, as explained herein with regard to previously described embodiments.

Still referring to FIG. 8, downstream apparatus 40 includes a roof 4, floor 6, and sidewall structure 8, as well as a port 20 fluidly connecting downstream apparatus 40 with SCM exit structure 56 and SCM 2. Dashed lines with one-headed arrows indicate measured density input signals 36, 37, 38, and 39, obtained using EM detectors 34A-E, which receive and measure intensity of attenuated EM radiation initially emitted by one or more EM sources (hidden from view in FIG. 8), and that have been attenuated by passing through two portions of sidewall structure 8 and molten foamed glass in downstream apparatus 40. Measured density input signals 36, 37, 38, and 39 are routed through wired or wireless connections to a master controller "MC", which may interface with a computer terminal 80 and optional printer 86 through wired (82) or wireless (84) connections. Master controller "MC" may compare measured density input signals 36, 37, 38, and 39 to set point values, and then emit appropriate output control signals 58, 60, 62, and 64, for example to adjust SCM feed rate using output signal 58, to adjust oxidant flow rate using output signal 60 and/or fuel flow rate using output signal 62, and SCM production rate of molten foamed glass using output signal 64. Flow adjusting valves and actuators for achieving the control functions are not illustrated for brevity, but would include appropriately sized and engineered valves and actuators for those valves. One or more slave controllers "SC" may receive measured density input signals 38, 39, and employ one or more control strategies to produce output control signals 66, 67, to control fuel and/or oxidant flow rate to one or more burners 24 protruding through roof 4 of downstream apparatus 40 for providing heat and/or foam control in downstream apparatus 40. Another output control signal 69 may be employed to control one or more optional electric coils 68 for Joule heating or temperature maintenance of molten foamed glass 14 in downstream apparatus 40. Joule heating may be preferred for example when it is desired to maintain a very dry atmosphere 18 above molten foamed glass 14, in situation when it is desired to produce foamed glass products. The oxidant "O" in SC burners 53, 55, and 57, and burners 24 may be selected from the group consisting of ambient air, synthetic air, oxygen-enriched ambient air, oxygen-enriched synthetic air, and compositions comprising more than about 95 mole percent oxygen.

Figure 12:
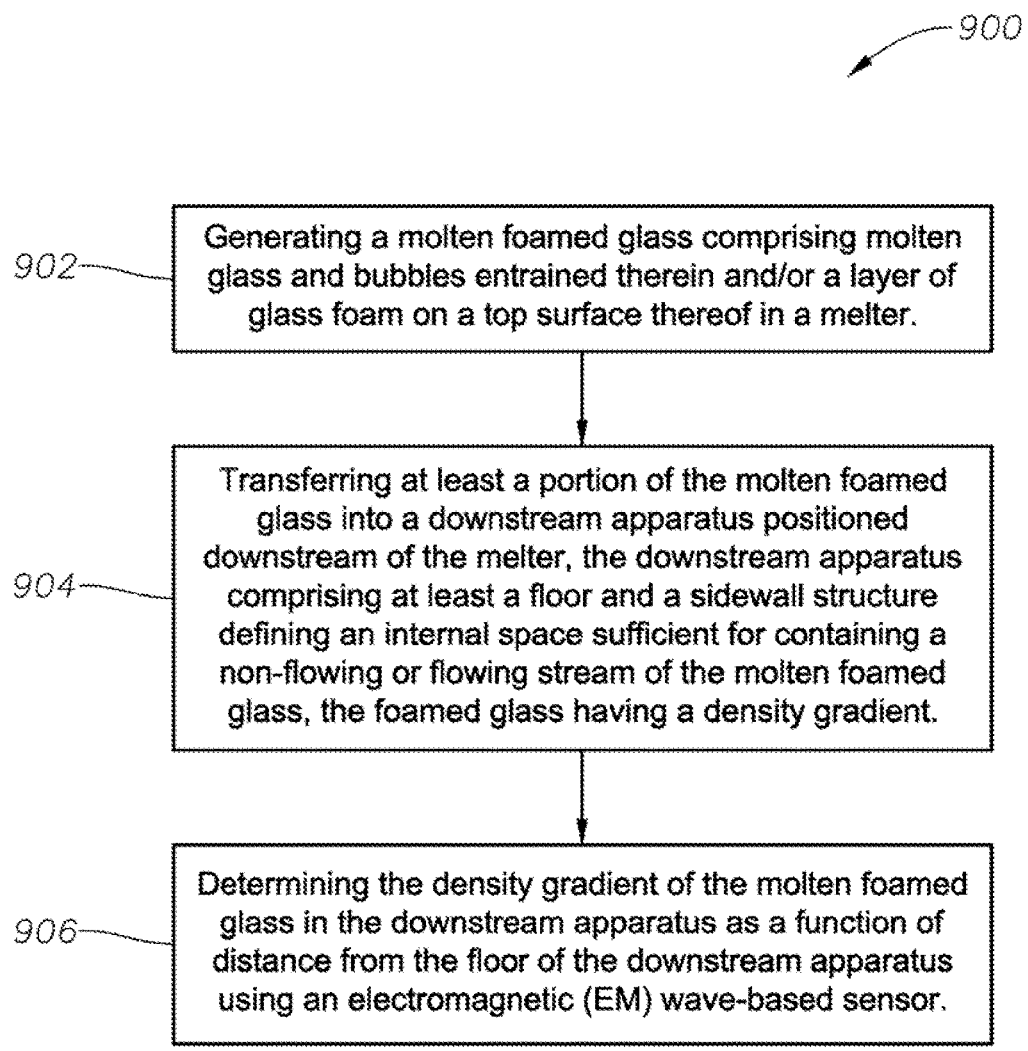
FIGS. 12 and 13 are logic diagrams of two methods in accordance with the present disclosure.
Figure 13:
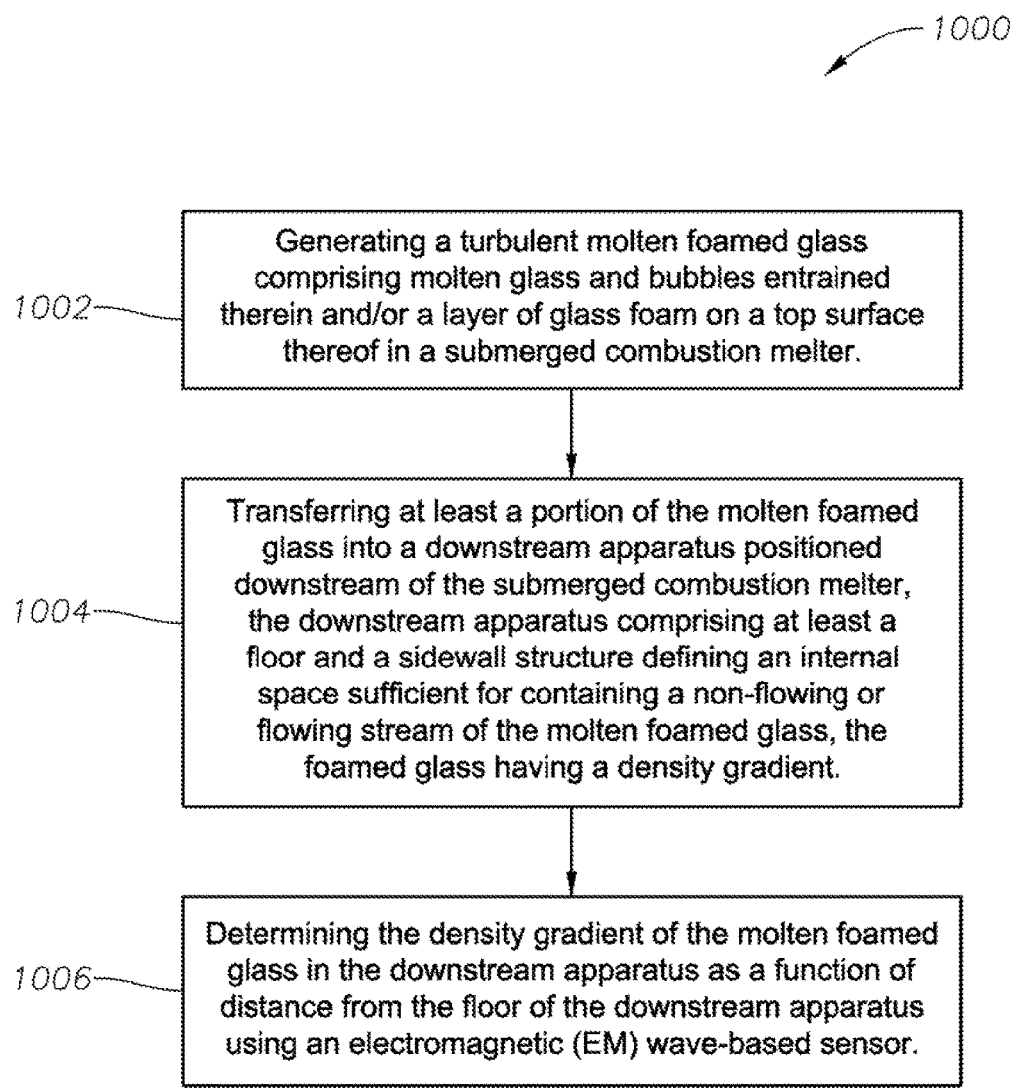

FIGS. 12 and 13 are logic diagrams of two method embodiments of the present disclosure. Method embodiment 900 of FIG. 12 includes the steps of generating a molten foamed glass comprising molten glass and bubbles entrained therein and/or a layer of glass foam on a top surface thereof in a melter, box 902, and then transferring at least a portion of the molten foamed glass into a downstream apparatus positioned downstream of the melter, the downstream apparatus comprising at least a floor and a sidewall structure defining an internal space sufficient for containing a non-flowing or flowing stream of the molten foamed glass, the foamed glass having a density gradient, box 904. The method further comprises determining the density gradient of the molten foamed glass in the downstream apparatus as a function of distance from the floor of the downstream apparatus using an electromagnetic (EM) wave-based sensor, box 906. Method embodiment 1000 comprises generating a turbulent molten foamed glass comprising molten glass and bubbles entrained therein and/or a layer of glass foam on a top surface thereof in a submerged combustion melter, box 1002, and then transferring at least a portion of the molten foamed glass into a downstream apparatus positioned downstream of the submerged combustion melter, the downstream apparatus comprising at least a floor and a sidewall structure defining an internal space sufficient for containing a non-flowing or flowing stream of the molten foamed glass, the foamed glass having a density gradient, box 1004. Method embodiment 1000 continues by determining the density gradient of the molten foamed glass in the downstream apparatus as a function of distance from the floor of the downstream apparatus using an electromagnetic (EM) wave-based sensor, box 1006.

SC burners in an SCM produce a turbulent melt comprising bubbles having a bubble atmosphere. In general the atmosphere of the bubbles is about the same from bubble to bubble, but that is not necessarily so. One or more burners in SCM 2 may be oxy-fuel burners. SCM 2 may receive numerous feeds through one or more inlet ports, and batch feeders maybe provided. Other feeds are possible, such as glass mat waste, wound roving, waste materials, and the like, such as disclosed in assignee's U.S. Pat. No. 8,650,914.

Fluids may be supplied from one or more supply tanks or containers which are fluidly and mechanically connected to the downstream apparatus via one or more conduits, which may or may not include flow control valves. One or more of the conduits may be flexible metal hoses, but they may also be solid metal, ceramic, or ceramic-lined metal conduits. Any or all of the conduits may include a flow control valve, which may be adjusted to shut off flow through a particular conduit.

In systems and methods employing glass batch as feed, such as embodiment 800 of FIG. 8, one or more hoppers 50 containing one or more particles or particulate matter may be provided. One or more hoppers may route particles through the SCM roof, through an SCM sidewall, or through both, through various apertures. While it is contemplated that particulate will flow merely by gravity from the hoppers, and the hoppers need not have a pressure above the solids level, certain embodiments may include a pressurized headspace above the solids in the hoppers. In embodiments, the teachings of assignee's co-pending application Ser. No. 13/540,704, filed Jul. 3, 2012, describing various screw-feeder embodiments, and teaching of feed material compaction may be useful. One or more of the hoppers may include shakers or other apparatus common in industry to dislodge overly compacted solids and keep the particles flowing. Furthermore, each hopper will have a valve other apparatus to stop or adjust flow of particulate matter into the downstream apparatus. These details are not illustrated for sake of brevity.

Certain systems and methods of the present disclosure may be combined with strategies for foam de-stabilization, if that is the desired end. For example, adding nitrogen as a treating composition to the molten mass of glass and bubbles in the downstream apparatus may tend to make bubbles in glass foam 16 less stable when there is the presence of a high moisture atmosphere in the downstream apparatus. A high moisture atmosphere may exist in the downstream apparatus for example when one or more high momentum burners (whether oxy/fuel or not) are used as impingement burners in the downstream apparatus to impinge on glass foam 16. The use of one or more high momentum impingement burners (whether oxy/fuel or not) in a downstream flow channel is described in assignee's U.S. Pat. No. 8,707,739.

The downstream apparatus may include one or more bushings 88 (FIG. 8) for example when producing glass fiber. Downstream apparatus for use in systems and methods of the present disclosure may comprise a roof, floor and sidewall structure comprised of an outer metal shell, non-glass-contact brick or other refractory wall, and glass-contact refractory for those portions expected to be in contact with molten glass. Downstream apparatus may include several sections arranged in series, each section having a roof, floor, and sidewall structure connecting its roof and floor, and defining a flow channel for conditioning molten glass flowing there through. The sections may be divided by a series of skimmers, each extending generally substantially vertically downward a portion of a distance between the roof and floor of the channel, with a final skimmer positioned between a last channel section and a forehearth. The number of sections and the number of skimmers may each be more or less than two. The downstream apparatus may be rectangular as illustrated in the various figures, or may be a shape such as a generally U-shaped or V-shaped channel or trough of refractory material supported by a metallic superstructure.

The flow rate of the molten glass through the downstream apparatus (unless it is a holding container without flow) will depend on many factors, including the geometry and size of the SCM and downstream apparatus, temperature of the melt, viscosity of the melt, and like parameters, but in general the flow rate of molten glass may range from about 0.5 lb./min to about 5000 lbs./min or more (about 0.23 kg/min to about 2300 kg/min or more), or from about 10 lbs./min to about 500 lbs./min (from about 4.5 kg/min to about 227 kg/min), or from about 100 lbs./min to 300 lbs./min (from about 45 kg/min to about 136 kg/min).

Certain embodiments may use low momentum burners for heat and/or foam de-stabilization in downstream apparatus 40. Low momentum burners useful in systems and methods of this disclosure may include some of the features of those disclosed in assignee's U.S. Pat. No. 9,021,838. For low momentum burners using natural gas as fuel, the burners may have a fuel firing rate ranging from about 0.4 to about 40 scfh (from about 11 L/hr. to about 1,120 L/hr.); an oxygen firing rate ranging from about 0.6 to about 100 scfh (from about 17 L/hr. to about 2,840 L/hr.); a combustion ratio ranging from about 1.5 to about 2.5; nozzle velocity ratio (ratio of velocity of fuel to oxygen at the fuel nozzle tip) ranging from about 0.5 to about 2.5; a fuel velocity ranging from about 6 ft./second to about 40 ft./second (about 2 meters/second to about 12 meters/second) and an oxidant velocity ranging from about 6 ft./second to about 40 ft./second (about 2 meters/second to about 12 meters/second).

Those of skill in this art will readily understand the need for, and be able to construct suitable fuel supply conduits and oxidant supply conduits, as well as respective flow control valves, threaded fittings, quick connect/disconnect fittings, hose fittings, and the like.

Submerged combustion melters may be fed a variety of feed materials. The initial raw material may include any material suitable for forming molten glass such as, for example, limestone, glass, sand, soda ash, feldspar and mixtures thereof. A glass composition for producing glass fibers known as "E-glass" typically includes 52-56% $SiO_2$, 12-16% $Al_2O_3$, 0-0.8% $Fe_2O_3$, 16-25% CaO, 0-6% MgO, 0-10% $B_2O_3$, 0-2% $Na_2O+K_2O$, 0-1.5% $TiO_2$ and 0-1% $F_2$. Other glass compositions may be used, such as those described in assignee's published U.S. applications 2007/0220922 and 2008/0276652. The initial raw material to provide these glass compositions can be calculated in known manner from the desired concentrations of glass components, molar masses of glass components, chemical formulas of batch components, and the molar masses of the batch components. Typical E-glass batches include those reproduced in Table 1, borrowed from the 2007/0220922 application. Notice that during glass melting, carbon dioxide (from lime) and water (borax) evaporate. The initial raw material can be provided in any form such as, for example, relatively small particles.

TABLE 1

A typical E-glass batch
BATCH COMPOSITION (BY WEIGHT)

| Raw material | Limestone (Baseline) | Quick-lime | Ca Silicate | Volcanic Glass | Ca Silicate & Volcanic Glass | Quartz-free #1 | Quartz-free #2 | Limestone Slag | Ca Silicate Slag | Quartz-free #3 | Quartz and Clay Free | Ca Silicate/ Feldspar |
|---|---|---|---|---|---|---|---|---|---|---|---|---|
| Quartz (flint) | 31.3% | 35.9% | 15.2% | 22.6% | 8.5% | 0% | 0% | 22.3% | 5.7% | 0% | 0% | 19.9% |
| Kaolin Clay | 28.1% | 32.3% | 32.0% | 23.0% | 28.2% | 26.4% | 0% | 22.7% | 26.0% | 26.0% | 0% | 0% |
| BD Lime | 3.4% | 4.3% | 3.9% | 3.3% | 3.8% | 3.7% | 4.3% | 2.8% | 3.1% | 3.1% | 4.3% | 4.4% |
| Borax | 4.7% | 5.2% | 5.2% | 0% | 1.5% | 0% | 0% | 0% | 0% | 0% | 1.1% | 1.1% |
| Boric Acid | 3.2% | 3.9% | 3.6% | 7.3% | 6.9% | 8.2% | 8.6% | 7.3% | 8.2% | 8.2% | 7.7% | 7.8% |
| Salt Cake | 0.2% | 0.2% | 0.2% | 0.2% | 0.2% | 0.2% | 0.2% | 0.2% | 0.2% | 0.2% | 0.2% | 0.2% |
| Limestone | 29.1% | 0% | 0% | 28.7% | 0% | 0% | 0% | 27.9% | 0% | 0% | 0% | 0% |
| Quicklime | 0% | 18.3% | 0% | 0% | 0% | 0% | 0% | 0% | 0% | 0% | 0% | 0% |
| Calcium Silicate | 0% | 0% | 39.9% | 0% | 39.1% | 39.0% | 27.6% | 0% | 37.9% | 37.9% | 26.5% | 26.6% |
| Volcanic Glass | 0% | 0% | 0% | 14.9% | 11.8% | 17.0% | 4.2% | 14.7% | 16.8% | 16.8% | 0% | 0% |
| Diatomaceous Earth (DE) | | | | | | 5.5% | 17.4% | 0% | 0% | 5.7% | 20.0% | 0% |
| Plagioclase Feldspar | | | | | | 0% | 38.3% | 0% | 0% | 0% | 40.1% | 40.1% |
| Slag | | | | | | 0% | 0% | 2.0% | 2.0% | 2.0% | 0% | 0% |
| Total | 100% | 100% | 100% | 100% | 100% | 100% | 100% | 100% | 100% | 100% | 100% | 100% |
| Volume of $CO_2$ @ 1400 C. | 1668 | 0 | 0 | 1647 | 0 | 0 | 0 | 1624 | 0 | 0 | 0 | 0 |

SCMs may also be fed by one or more roll stands, which in turn supports one or more rolls of glass mat, as described in assignee's U.S. Pat. No. 8,650,914, incorporated herein by reference. In certain embodiments powered nip rolls may include cutting knives or other cutting components to cut or chop the mat (or roving, in those embodiments processing roving) into smaller length pieces prior to entering the SCM. Also provided in certain embodiments may be a glass batch feeder. Glass batch feeders are well-known in this art and require no further explanation.

Downstream apparatus and melters such as SCMs may include refractory fluid-cooled panels. Liquid-cooled panels may be used, having one or more conduits or tubing therein, supplied with liquid through one conduit, with another conduit discharging warmed liquid, routing heat transferred from inside the melter to the liquid away from the melter. Liquid-cooled panels may also include a thin refractory liner, which minimizes heat losses from the melter, but allows formation of a thin frozen glass shell to form on the surfaces and prevent any refractory wear and associated glass contamination. Other useful cooled panels include air-cooled panels, comprising a conduit that has a first, small diameter section, and a large diameter section. Warmed air transverses the conduits such that the conduit having the larger diameter accommodates expansion of the air as it is warmed. Air-cooled panels are described more fully in U.S. Pat. No. 6,244,197. In certain embodiments, the refractory fluid cooled-panels are cooled by a heat transfer fluid selected from the group consisting of gaseous, liquid, or combinations of gaseous and liquid compositions that functions or is capable of being modified to function as a heat transfer fluid. Gaseous heat transfer fluids may be selected from air, including ambient air and treated air (for air treated to remove moisture), inert inorganic gases, such as nitrogen, argon, and helium, inert organic gases such as fluoro-, chloro- and chlorofluorocarbons, including perfluorinated versions, such as tetrafluoromethane, and hexafluoroethane, and tetrafluoroethylene, and the like, and mixtures of inert gases with small portions of non-inert gases, such as hydrogen. Heat transfer liquids may be selected from inert liquids that may be organic, inorganic, or some combination thereof, for example; salt solutions, glycol solutions, oils and the like. Other possible heat transfer fluids include steam (if cooler than the oxygen manifold temperature), carbon dioxide, or mixtures thereof with nitrogen. Heat transfer fluids may be compositions comprising both gas and liquid phases, such as the higher chlorofluorocarbons.

As noted in the discussion of embodiment 800 (FIG. 8), certain embodiments may comprise a method control scheme for the downstream apparatus and/or SCM. For example, as explained in the '914 patent, a master method controller may be configured to provide any number of control logics, including feedback control, feed-forward control, cascade control, and the like. The disclosure is not limited to a single master method controller, as any combination of controllers could be used. The term "control", used as a transitive verb, means to verify or regulate by comparing with a standard or desired value. Control may be closed loop, feedback, feed-forward, cascade, model predictive, adaptive, heuristic and combinations thereof. The term "controller" means a device at least capable of accepting input from sensors and meters in real time or near-real time, and sending commands directly to one or more control elements, and/or to local devices associated with control elements able to accept commands. A controller may also be capable of accepting input from human operators; accessing databases, such as relational databases; sending data to and accessing data in databases, data warehouses or data marts; and sending information to and accepting input from a display device readable by a human. A controller may also interface with or have integrated therewith one or more software application modules, and may supervise interaction between databases and one or more software application modules. The controller may utilize Model Predictive Control (MPC) or other advanced multivariable control methods used in multiple input/multiple output (MIMO) systems. As mentioned previously, the methods of assignee's U.S. Pat. No. 8,973,400, using the vibrations and oscillations of the melter itself, may prove useful predictive control inputs.

The downstream apparatus and/or melter floors and sidewall structures may include a glass-contact refractory lining. The glass-contact lining may be 1 centimeter, 2 centimeters, 3 centimeters or more in thickness, however, greater thickness may entail more expense without resultant greater benefit. The refractory lining may be one or multiple layers. Glass-contact refractory used in downstream apparatus described herein may be fused cast materials based on AZS (alumina-zirconia-silica), $\alpha/\beta$ alumina, zirconium oxide, chromium oxide, chrome corundum, end the like available from RHI AG, Vienna, Austria under the trade names MONOFRAX and REFEL, or refractory mixes such as those known under the trade names COMPAC, COMPRIT, SUPER COMPRIT, SPEEDCAST, and the like, also available from RHI AG. As disclosed in U.S. Pat. No. 4,323,718, two layers may be applied, the first being a hydraulically setting insulating composition. This composition may be poured in a form of a wall section of desired thickness, for example a layer 5 cm thick, or 10 cm, or greater. This material is allowed to set, followed by a second layer of a hydraulically setting refractory casting composition may be applied thereonto. Other suitable materials for components that require resistance to high temperatures are fused zirconia ($ZrO_2$), fused cast AZS (alumina-zirconia-silica), rebonded AZS, or fused cast alumina ($Al_2O_3$). The choice of a particular material is dictated among other parameters by the geometry of the flow channel or other equipment and the type of glass being produced.

Those having ordinary skill in this art will appreciate that there are many possible variations of the systems and methods described herein, and will be able to devise alternatives and improvements to those described herein that are nevertheless considered to be within the claims.

What is claimed is:

1. A system comprising:
   a submerged combustion melter comprising a floor, a roof, and a melter sidewall structure connecting the floor and roof, the melter having an intermediate location comprising a constant width zone positioned between an expanding width zone and a narrowing width zone, the melter configured to define an internal space for generating a turbulent molten foamed glass, the submerged combustion melter comprising at least one combustion burner positioned in the floor, the roof, and/or the sidewall structure from which emanates combustion products that intimately contact the molten foamed glass and provide the turbulent molten foamed glass;
   a downstream apparatus positioned downstream of and fluidly connected to the submerged combustion melter, the downstream apparatus comprising at least a floor and a sidewall structure defining an internal space sufficient for containing a non-flowing or flowing stream of the molten foamed glass;
   two or more electromagnetic (EM) wave sources selected from the group consisting of nuclear and X-ray sources supported by two or more first stationary, substantially vertical posts adjacent a first sidewall portion of the melter and the downstream apparatus, and two or more EM wave detectors selected from the group consisting of nuclear and X-ray detectors supported by two or more second stationary, substantially vertical posts adjacent an opposite sidewall portion of the melter and the downstream apparatus, the two or more detectors positioned to intercept an attenuated EM wave;

the two or more first and second stationary, substantially vertical posts extending generally vertically from a plant floor or other support structure up to points along portions of external surfaces of the respective first and opposite sidewall portions;

the two or more first and second stationary, substantially vertical posts extending to respective heights that are less than, equal to, or greater than a height of the melter or downstream apparatus roof;

the two or more EM wave sources supported by the two or more first stationary, substantially vertical posts adjacent the first sidewall portion of the melter and the downstream apparatus, and the two or more EM wave detectors supported by the two or more second stationary, substantially vertical posts adjacent the opposite sidewall portion of the melter and downstream apparatus, configured to determine change of density of the molten foamed glass at a given depth in the melter and the downstream apparatus, or both as a function of time.

2. The system of claim 1 wherein the two or more EM wave sources comprises a plurality of stationary EM wave sources arranged vertically on respective single stationary, substantially vertical posts adjacent the first sidewall portion of the melter and the downstream apparatus, and the two or more EM wave detectors comprises a plurality of stationary EM wave detectors arranged vertically on respective single stationary, substantially vertical posts adjacent the opposite sidewall portion of the melter and the downstream apparatus, or both.

3. The system of claim 1 wherein the two or more EM wave sources are respective single EM wave sources vertically positionable on respective single stationary, substantially vertical posts adjacent the first sidewall portion of the melter and the downstream apparatus, and the two or more EM wave detectors comprises a plurality of stationary EM wave detectors arranged vertically on respective single stationary, substantially vertical posts adjacent the opposite sidewall portion of the melter and the downstream apparatus.

4. The system of claim 1 wherein the two or more EM wave sources are respective single EM wave sources vertically pivotally mounted on respective single stationary, substantially vertical posts adjacent the first sidewall portion of the melter and the downstream apparatus, and the two or more EM wave detectors comprises a plurality of stationary EM wave detectors arranged vertically on respective single stationary, substantially vertical posts adjacent the opposite sidewall portion of the melter and the downstream apparatus.

5. The system of claim 1 wherein the two or more EM wave detectors are respective single EM wave detectors vertically positionable on respective single stationary, substantially vertical posts adjacent the opposite sidewall portion of the melter and the downstream apparatus, and the two or more EM wave sources comprises respective pluralities of stationary EM wave sources arranged vertically on respective single stationary, substantially vertical posts adjacent the first sidewall portion of the melter and the downstream apparatus.

6. The system of claim 1 wherein the two or more EM wave detectors are respective single EM wave detectors vertically pivotally mounted on respective single stationary, substantially vertical posts adjacent the opposite sidewall portion of the melter and the downstream apparatus, and the two or more EM wave sources comprises respective pluralities of stationary EM wave sources arranged vertically on respective single stationary, substantially vertical posts adjacent the first sidewall portion of the melter and the downstream apparatus.

7. The system of claim 1 wherein the two or more EM wave detectors are configured to produce two or more measured density input signals routed through wired or wireless connections to a master controller that interfaces with a computer through wired or wireless connections, the master controller configured to compare the two or more measured density input signals to set point values, and then emit appropriate output control signals to adjust a parameter selected from the group consisting of melter feed rate, submerged combustion burner oxidant flow rate, submerged combustion fuel flow rate, production rate of molten foamed glass, and combinations thereof, and one or more slave controllers configured to receive two or more measured density input signals and employ one or more control strategies to produce two or more output control signals to control fuel and/or oxidant flow rate to one or more foam impingement burners protruding through the roof of the downstream apparatus for providing foam control in the downstream apparatus, and optionally another output control signal configured to control one or more optional electric coils for Joule heating or temperature maintenance of molten foamed glass in the downstream apparatus.

8. The system of claim 1 wherein the two or more EM sources and detectors are positioned to measure the density of the molten foamed glass near an expected interface between glass foam and liquid molten glass in the melter and the downstream apparatus.

9. A system comprising:
  a submerged combustion melter comprising a floor, a roof, and a melter sidewall structure connecting the floor and roof, the melter having an intermediate location comprising a constant width zone positioned between an expanding width zone and a narrowing width zone, the melter configured to define an internal space for generating a turbulent molten foamed glass, the submerged combustion melter comprising at least one combustion burner positioned in the floor, the roof, and/or the sidewall structure from which emanates combustion products that intimately contact the molten foamed glass and provide the turbulent molten foamed glass;
  a downstream apparatus positioned downstream of and fluidly connected to the submerged combustion melter, the downstream apparatus comprising at least a floor and a sidewall structure defining an internal space sufficient for containing a non-flowing or flowing stream of the molten foamed glass; and
  two or more electromagnetic (EM) wave sources selected from the group consisting of nuclear and X-ray sources supported by two or more first substantially vertical portions of respective stationary frames, the two or more first substantially vertical portions of the respective frames adjacent respective first sidewall portions of the melter and the downstream apparatus, and two or more EM wave detectors selected from the group consisting of nuclear and X-ray detectors supported by two or more second substantially vertical portions of the respective stationary frames, the two or more second substantially vertical portions of the respective frames adjacent an opposite sidewall portion of the melter and the downstream apparatus, the two or more EM wave detectors positioned to intercept an attenuated EM wave;

the two or more electromagnetic (EM) wave sources supported by the two or more first substantially vertical portions of the respective stationary frames, the first substantially vertical portions of the respective frames adjacent the first sidewall portion of the melter and the downstream apparatus, and the two or more EM wave detectors supported by the two or more second substantially vertical portions of the respective stationary frames, the second substantially vertical portions of the respective frames adjacent the opposite sidewall portions of the melter and the downstream apparatus, or both, configured to determine change of density of the molten foamed glass at a given depth in either the melter, and in the downstream apparatus as a function of time.

10. The system of claim 9 wherein the two or more EM wave sources comprises respective pluralities of stationary EM wave sources arranged vertically on respective single stationary, substantially vertical first portions of the stationary frames adjacent the first sidewall portion of the melter and the downstream apparatus, or both, and the two or more EM wave detectors comprises respective pluralities of stationary EM wave detectors arranged vertically on respective single stationary, substantially vertical second portions of the respective stationary frames adjacent the opposite sidewall portions of the melter and the downstream apparatus.

11. The system of claim 9 wherein the two or more EM wave sources are respective single EM wave sources vertically positionable on respective single stationary, substantially vertical first portions of the respective stationary frames adjacent the first sidewall portions of the melter and the downstream apparatus, and the two or more EM wave detectors comprises a plurality of stationary EM wave detectors arranged vertically on a single stationary, substantially vertical second portion of the stationary frame adjacent the opposite sidewall portion of the melter or downstream apparatus, or both.

12. The system of claim 9 wherein the two or more EM wave sources are respective single EM wave sources vertically pivotally mounted on respective single stationary, substantially vertical first portions of the respective stationary frames adjacent the first sidewall portion of the melter and the downstream apparatus, and the two or more EM wave detectors comprises a plurality of stationary EM wave detectors arranged vertically on respective single stationary, substantially vertical second portions of the respective stationary frames adjacent the opposite sidewall portions of the melter and the downstream apparatus.

13. The system of claim 9 wherein the two or more EM wave detectors are respective single EM wave detectors vertically positionable on respective single stationary, substantially vertical first portions of the respective stationary frames adjacent the opposite sidewall portions of the melter and the downstream apparatus, and the two or more EM wave sources comprises respective pluralities of stationary EM wave sources arranged vertically on respective single stationary, substantially vertical second portions of the stationary frames adjacent the first sidewall portions of the melter and the downstream apparatus.

14. The system of claim 9 wherein the two or more EM wave detectors are respective single EM wave detectors vertically pivotally mounted on respective single stationary, substantially vertical first portions of the respective stationary frames adjacent the opposite sidewall portions of the melter and the downstream apparatus, and the two or more EM wave sources comprises respective pluralities of stationary EM wave sources arranged vertically on respective single stationary, substantially vertical second portions of the stationary frames adjacent the first sidewall portions of the melter and the downstream apparatus.

15. The system of claim 9 wherein the two or more EM wave detectors are configured to produce two or more measured density input signals routed through wired or wireless connections to a master controller that interfaces with a computer through wired or wireless connections, the master controller configured to compare the two or more measured density input signals to set point values, and then emit appropriate output control signals to adjust a parameter selected from the group consisting of melter feed rate, submerged combustion burner oxidant flow rate, submerged combustion fuel flow rate, production rate of molten foamed glass, and combinations thereof, and one or more slave controllers configured to receive two or more measured density input signals and employ one or more control strategies to produce two or more output control signals to control fuel and/or oxidant flow rate to one or more foam impingement burners protruding through the roof of the downstream apparatus for providing foam control in the downstream apparatus, and optionally another output control signal configured to control one or more optional electric coils for Joule heating or temperature maintenance of molten foamed glass in the downstream apparatus.

16. The system of claim 9 wherein the two or more EM sources and detectors are positioned to measure the density of the molten foamed glass near an expected interface between glass foam and liquid molten glass in the melter and the downstream apparatus.

17. A system comprising:
a submerged combustion melter comprising a floor, a roof, and a melter sidewall structure connecting the floor and roof, the melter having an intermediate location comprising a constant width zone positioned between an expanding width zone and a narrowing width zone, the melter configured to define an internal space for generating a turbulent molten foamed glass, the submerged combustion melter comprising at least one combustion burner positioned in the floor, the roof, and/or the sidewall structure from which emanates combustion products that intimately contact the molten foamed glass and provide the turbulent molten foamed glass;
a downstream apparatus positioned downstream of and fluidly connected to the submerged combustion melter, the downstream apparatus comprising at least a floor and a sidewall structure defining an internal space sufficient for containing a non-flowing or flowing stream of the molten foamed glass;
two or more electromagnetic (EM) wave sources selected from the group consisting of nuclear and X-ray sources supported by two or more first substantially vertical portions of respective movable frames, the first substantially vertical portions of the respective frames adjacent a first sidewall portion of the melter and the downstream apparatus, and two or more EM wave detectors selected from the group consisting of nuclear and X-ray detectors supported by two or more second substantially vertical portions of the respective movable frames, the second substantially vertical portions of the respective frames adjacent an opposite sidewall portion of the melter and the downstream apparatus, the two or more detectors positioned to intercept respective attenuated EM waves;

the two or more electromagnetic (EM) wave sources supported by the two or more first substantially vertical portions of the respective movable frames, the first substantially vertical portions of the respective frames adjacent the first sidewall portion of the melter and the downstream apparatus, or both, and the two or more EM wave detectors supported by the two or more second substantially vertical portions of the respective movable frames, the second substantially vertical portions of the respective frames adjacent the opposite sidewall portions of the melter and the downstream apparatus, configured to determine change of density of the molten foamed glass at a given depth in the melter, and the downstream apparatus, as a function of time;

configured to determine change of density of the molten foamed glass at a given depth in the melter, and the downstream apparatus as a function of time.

18. The system of claim 17 wherein the two or more EM wave sources each comprises respective pluralities of EM wave sources arranged vertically on respective single movable, substantially vertical first portions of the respective movable frames adjacent the respective first sidewall portions of the melter and the downstream apparatus, or both, and the two or more EM wave detectors each comprises respective pluralities of EM wave detectors arranged vertically on respective single movable, substantially vertical second portions of the respective movable frames adjacent the respective opposite sidewall portions of the melter and the downstream apparatus.

19. The system of claim 17 wherein the two or more EM wave sources are respective single EM wave sources vertically positionable on the respective single movable, substantially vertical first portions of the respective movable frames adjacent the respective first sidewall portions of the melter and the downstream apparatus, and the two or more EM wave detectors comprises respective pluralities of EM wave detectors arranged vertically on respective single movable, substantially vertical second portions of the movable frames adjacent the respective opposite sidewall portions of the melter and the downstream apparatus.

20. The system of claim 17 wherein the two or more EM wave sources are respective single EM wave sources vertically pivotally mounted on respective single movable, substantially vertical first portions of the respective movable frames adjacent the respective first sidewall portions of the melter and the downstream apparatus, and the two or more EM wave detectors comprises respective pluralities of EM wave detectors arranged vertically on the respective single movable, substantially vertical second portions of the movable frames adjacent the opposite sidewall portions of the melter and the downstream apparatus.

21. The system of claim 17 wherein the two or more EM wave detectors are respective single EM wave detectors vertically positionable on respective single movable, substantially vertical first portions of the respective movable frames adjacent the respective opposite sidewall portions of the melter and the downstream apparatus, and the two or more EM wave sources comprises respective pluralities of EM wave sources arranged vertically on respective single movable, substantially vertical second portions of the movable frames adjacent the first sidewall portions of the melter and the downstream apparatus, or both.

22. The system of claim 17 wherein the two or more EM wave detectors are respective single EM wave detectors vertically pivotally mounted on respective single movable, substantially vertical first portions of the respective movable frames adjacent the opposite sidewall portions of the melter and the downstream apparatus, and the two or more EM wave sources comprises respective pluralities of EM wave sources arranged vertically on respective single movable, substantially vertical second portions of the respective movable frames adjacent the first sidewall portions of the melter and the downstream apparatus.

23. The system of claim 17 wherein the two or more EM wave detectors are configured to produce two or more measured density input signals routed through wired or wireless connections to a master controller that interfaces with a computer through wired or wireless connections, the master controller configured to compare the two or more measured density input signals to set point values, and then emit appropriate output control signals to adjust a parameter selected from the group consisting of melter feed rate, submerged combustion burner oxidant flow rate, submerged combustion fuel flow rate, production rate of molten foamed glass, and combinations thereof, and one or more slave controllers configured to receive two or more measured density input signals and employ one or more control strategies to produce two or more output control signals to control fuel and/or oxidant flow rate to one or more burners protruding through the roof of the downstream apparatus for providing foam control in the downstream apparatus, and optionally another output control signal configured to control one or more optional electric coils for Joule heating or temperature maintenance of molten foamed glass in the downstream apparatus.

24. The system of claim 17 wherein the two or more EM sources and detectors are positioned to measure the density of the molten foamed glass near an expected interface between glass foam and liquid molten glass in the melter and the downstream apparatus.

\* \* \* \* \*